(12) United States Patent
Sridharan et al.

(10) Patent No.: US 11,554,958 B2
(45) Date of Patent: Jan. 17, 2023

(54) ULTRA-SOFT COATINGS FOR INTERFACES WITH BRAIN AND OTHER SOFT TISSUES

(71) Applicant: Arizona Board of Regents on behalf of Arizona State University, Scottsdale, AZ (US)

(72) Inventors: Arati Sridharan, Chandler, AZ (US); Jitendran Muthuswamy, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 738 days.

(21) Appl. No.: 16/322,759

(22) PCT Filed: Aug. 4, 2017

(86) PCT No.: PCT/US2017/045470
§ 371 (c)(1),
(2) Date: Feb. 1, 2019

(87) PCT Pub. No.: WO2018/027117
PCT Pub. Date: Feb. 8, 2018

(65) Prior Publication Data
US 2021/0331925 A1  Oct. 28, 2021

Related U.S. Application Data

(60) Provisional application No. 62/370,836, filed on Aug. 4, 2016.

(51) Int. Cl.
*C01B 32/174* (2017.01)
*C08K 3/04* (2006.01)
(Continued)

(52) U.S. Cl.
CPC ............ *C01B 32/174* (2017.08); *C08K 3/041* (2017.05); *C09D 7/61* (2018.01); *H01B 1/24* (2013.01); *A61B 5/686* (2013.01)

(58) Field of Classification Search
CPC .................................................... C01B 32/174
See application file for complete search history.

(56) References Cited

U.S. PATENT DOCUMENTS 4,343,788 A * 8/1982 Mustacich ............. A61P 31/00
514/578
5,741,877 A   4/1998 Tiffany
(Continued)

FOREIGN PATENT DOCUMENTS

WO   2018027117 A1   2/2018
WO   2020160455 A1   8/2020

OTHER PUBLICATIONS

Prasad, A. et al., "Quantifying long-term microelectrode array functionality using chronic impedance testing", Journal of Neural Engineering, Mar. 2012, vol. 9, article 026028, 12 pages <DOI:10.1088/1741-2560/9/2/026028>.

(Continued)

*Primary Examiner* — William D Young
(74) *Attorney, Agent, or Firm* — Lewis Roca Rothgerber Christie LLP

(57) ABSTRACT

A soft conductive composition can include: a crosslinked silicone composition; and single-walled or multi-walled carbon nanotubes in the silicone composition. A neural probe or other implant can include the soft conducive composition on a least a portion of the implant body. A method of making an implant can include: selecting PDMS precursors; cross-linking the PDMS precursor to obtain an elastic modulus of about 3-9 kPa or +/−1%, 5%, 10%, 20%, or 50%; selecting the carbon nanotubes; introducing the carbon nanotubes into the crosslinked PDMS to form a soft (Continued)

conductive composite composition; and coating the soft conductive composite composition onto at least a portion of an implant. A method of measuring properties at a neural interface can include: providing a neural probe having a soft conductive composition; implanting the neural probe having the soft conductive composition at a neural interface; and measuring a property with the neural probe.

20 Claims, 11 Drawing Sheets

(51) Int. Cl.
    *C09D 7/61*     (2018.01)
    *H01B 1/24*     (2006.01)
    *A61B 5/00*     (2006.01)

(56) References Cited

U.S. PATENT DOCUMENTS

| | | | |
|---|---|---|---|
| 10,589,124 B2 | 3/2020 | Smith et al. | |
| 10,835,184 B2 | 11/2020 | Muthuswamy et al. | |
| 10,974,065 B2 | 4/2021 | Smith et al. | |
| 2009/0038820 A1 | 2/2009 | Keefer | |
| 2011/0129925 A1 | 6/2011 | Yan et al. | |
| 2012/0301360 A1* | 11/2012 | Meinhold | G01N 1/405 |
| | | | 422/68.1 |
| 2014/0127490 A1* | 5/2014 | Islam | C08K 7/24 |
| | | | 428/219 |
| 2014/0291589 A1* | 10/2014 | Hata | C01B 32/16 |
| | | | 252/511 |
| 2015/0054348 A1* | 2/2015 | Akiya | H02J 50/10 |
| | | | 307/104 |
| 2015/0202351 A1* | 7/2015 | Kaplan | A61B 5/6877 |
| | | | 607/116 |
| 2019/0247668 A1 | 8/2019 | Towe et al. | |
| 2021/0121129 A1 | 4/2021 | Muthuswamy et al. | |

OTHER PUBLICATIONS

Sankar, V. et al., "Electrode impedance analysis of chronic tungsten microwire neural implants: understanding abiotic vs. biotic contributions", Frontiers in Neuroengineering, May 2014, vol. 7, article 13, 12 pages <DOI:10.3389/fneng.2014.00013>.

Seidlits, S. et al., "The effects of hyaluronic acid hydrogels with tunable mechanical properties on neural progenitor cell differentiation", Biomaterials, May 2010, vol. 31, No. 14, pp. 3930-3940 <DOI:10.1016/j.biomaterials.2010.01.125>.

Seymour, J. et al., "Neural probe design for reduced tissue encapsulation in CNS", Biomaterials, Sep. 2007, vol. 28, No. 25, pp. 3594-3607 <DOI:10.1016/j.biomaterials.2007.03.024>.

Shen, W. et al., "Extracellular matrix-based intracortical microelectrodes: Toward a microfabricated neural interface based on natural materials", Microsystems & Nanoengineering, Jun. 2015, vol. 1, article 15010, 12 pages <DOI:10.1038/micronano.2015.10>.

Sokolov, I., "Atomic Force Microscopy in Cancer Cell Research", Cancer Nanotechnology, American Scientific Publishers, 2006, Ch. 1, pp. 1-17.

Spedden, E. et al., "Elasticity Maps of Living Neurons Measured by Combined Fluorescence and Atomic Force Microscopy", Biophysical Journal, Sep. 2012, vol. 103, pp. 868-877 <DOI:10.1016/j.bpj.2012.08.005>.

Sridharan, A. et al., "Compliant intracortical implants reduces strains and strain rates in brain tissue in vivo", Journal of Neural Engineering, Apr. 2015, vol. 12, article 036002, 12 pages <DOI:10.1088/1741-2560/12/3/036002>.

Sridharan, A. et al., "Gel-based Mimics for Tissue-Electrode Interfaces in the Brain Under Chronic Conditions", 2013, <URL:http://neuro.embs.org/files/2013/0670_FI.pdf>.

Sridharan, A. et al., "Long-term changes in the material properties of brain tissue at the implant-tissue interface", Journal of Neural Engineering, Oct. 2013, vol. 10, article 066001, 16 pages <DOI:10.1088/1741-2560/10/6/066001>.

Sridharan, A. et al., "Soft, brain-like neural interfaces yield stable electrical impedances in long-term experiments", presented at IEEE EMBS BRAIN Grand Challenges Conference, Nov. 13-14, 2014, Washington, D.C.

Stice, P, et al., "Assessment of gliosis around moveable implants in the brain", Journal of Neural Engineering, Jun. 2009, vol. 6, article 046004, 10 pages <DOI:10.1088/1741-2560/6/4/046004>.

Stiegliiz, .T et al., "Miniaturized neural interfaces and implants", Proceedings of SPIE, Feb. 2012, vol. 8251, article 82510A, 13 pages <DOI:10.1117/12.912526>.

Subbaroyan, J. et al., "A finite-element model of the mechanical effects of implantable microelectrodes in the cerebral cortex", Journal of Neural Engineering, Oct. 2005, vol. 2, No. 4, pp. 103-113 <DOI: 10.1088/1741-2560/2/4/006>.

Sugimoto, M. et al., "What is the nature of pancreatic consistency? Assessment of the elastic modulus of the pancreas and comparison with tactile sensation, histology, and occurrence of postoperative pancreatic fistula after pancreaticoduodenectomy", Surgery, Nov. 2014, vol. 156, No. 5, pp. 1204-1211 <DOI:10.1016/j.surg.2014.05.015>.

Suner, S. et al., "Reliability of Signals From a Chronically Implanted, Silicon-Based Electrode Array in Non-Human Primate Primary Motor Cortex", IEEE Transactions on Neural Systems and Rehabilitation Engineering, Dec. 2005, vol. 13, No. 4, pp. 524-541 <DOI:10.1109/TNSRE.2005.857687>.

Teixeira, A. et al., "The promotion of neuronal maturation on soft substrates", Biomaterials, Sep. 2009, vol. 30, No. 27, pp. 4567-4572 <DOI:10.1016/j.biomaterials.2009.05.013>.

Tunc, M. et al., "Reversible thermosensitive glue for retinal implants", Retina, Sep. 2007, vol. 27, No. 7, pp. 938-942 <DOI:10.1097/IAE.0b013e318042ae81>.

Vitale, F. et al., "Neural Stimulation and Recording with Bidirectional, Soft Carbon Nanotube Fiber Microelectrodes", ACS Nano, Mar. 2015, vol. 9, No. 4, pp. 4465-4474 <DOI:10.1021/acsnano.5b01060>.

Vlachopoulou, M. et al., "Effect of surface nanostructuring of PDMS on wetting properties, hydrophobic recovery, and protein adsorption", Microelectronic Engineering, Apr.-Jun. 2009, vol. 86, No. 4-6, pp. 1321-1324 <DOI:10.1016/j.mee.2008.11.050>.

Wang, Z. et al., "Crosslinking Effect on Polydimethylsiloxane Elastic Modulus Measured by Custom-Built Compression Instrument", Journal of Applied Polymer Science, 2014, article 41050, 4 pages <DOI:10.1002/APP.41050>.

Ware, T. et al., "Thiol-ene/acrylate substrates for softening intracortical electrodes", Journal of Biomedical Materials Research. Part B Applied Biomaterials, Jan. 2014 (available online May 2013), vol. 102, No. 1, pp. 1-11 <DOI:10.1002/jbmb.32946>.

Williams, J. et al., "Complex impedance spectroscopy for monitoring tissue responses to inserted neural implants", Journal of Neural Engineering, Nov. 2007, vol. 4, No. 4, pp. 410-423 <DOI:10.1088/1741-2560/4/4/007>.

Winslow, B. et al., "A comparison of the tissue response to chronically implanted Parylene-C-coated and uncoated planar silicon microelectrode arrays in rat cortex", Biomaterials, Dec. 2010, vol. 31, No. 35, pp. 9163-9172 <DOI:10.1016/j.biomaterials.2010.05.050>.

Yang, J. et al., "Microporous conducting polymers on neural microelectrode arrays I Electrochemical deposition", Sensors and Actuators B: Chemical, Jun. 2004, vol. 101, No. 1-2, pp. 133-142 <DOI:10.1016/j.snb.2004.02.056>.

U.S. Appl. No. 17/196,324, filed Mar. 9, 2021, Muthuswamy et al.
U.S. Appl. No. 17/225,711, filed Apr. 8, 2021, Smith et al.

Arreaga-Salas, D. et al., "Integration of High-Charge-Injection-Capacity Electrodes onto Polymer Softening Neural Interfaces", ACS Applied Materials & Interfaces, Nov. 2015, vol. 7, No. 48, pp. 26614-26623 <DOI:10.1021/acsami.5b08139>.

Barrese, J. et al., "Failure mode analysis of silicon-based intracortical microelectrode arrays in non-human primates", Journal of

(56) References Cited

OTHER PUBLICATIONS

Neural Engineering, Nov. 2013, vol. 10, article 066014, 23 pages <DOI: 10.1088/1741-2560/10/6/066014>.
Bianco, S. et al., "Nanocomposites Based on Elastomeric Matrix Filled with Carbon Nanotubes for Biological Applications", Carbon Nanotubes: From Research to Applications, Jul. 2011, Ch. 15, pp. 243-268 <DOI:10.5772/18638>.
Chen, H. et al., "Silicone elastomers for reduced protein adsorption", Biomaterials, May 2004, vol. 25, No. 12, pp. 2273-2282 <DOI:10.1016/j.biomaterials.2003.09.023>.
Cheung, K., "Implantable microscale neural interfaces", Biomed Microdevices, Jan. 2007, vol. 9, pp. 923-938 <DOI:10.1007/s10544-006-9045-z>.
Cui, X. et al., "In vivo studies of polypyrrole/peptide coated neural probes", Biomaterials, Feb. 2003, vol. 24, No. 5, pp. 777-787 <DOI:10.1016/S0142-9612(02)00415-5>.
Efimenko, K. et al., "Surface Modification of Sylgard-184 Poly(dimethyl siloxane) Networks by Ultraviolet and Ultraviolet/Ozone Treatment", Journal of Colloid and Interface Science, Oct. 2002, vol. 254, No. 2, pp. 306-315 <DOI:10.1006/jcis.2002.8594>.
Fernández, E. et al., "Acute human brain responses to intracortical microelectrode arrays: challenges and future prospects", Frotiers in Neuroengingeering, Jul. 2014, vol. 7, article 24, 6 pages <DOI:10.3389/fneng.2014.00024>.
Gilletti, A. et al., "Brain micromotion around implants in the rodent somatosensory cortex", Journal of Neural Engineering, Jun. 2006, vol. 3, pp. 189-195 <DOI:10.1088/1741-2560/3/3/001>.
Goodman, S. et al., "The future of biologic coatings for orthopaedic implants", Biomaterials, Apr. 2013, vol. 34, No. 13, pp. 3174-3183 <DOI:10.1016/j.biomaterials.2013.01.074>.
Graudejus, O. et al., "Encapsulating elastically stretchable neural interfaces: Yield, resolution, and recording/stimulation of neural activity", Advanced Functional Materials, Feb. 2012, vol. 22, No. 3, pp. 640-651 <DOI:10.1002/adfm.201102290>.
Gunasekera, B. et al., "Intracortical recording interfaces: Current challenges to chronic recording function", ACS Chemical Neuroscience, Jan. 2015, vol. 6, No. 1, pp. 68-83 <DOI:10.1021/cn5002864>.
Guo, L. et al., "A PDMS-Based Integrated Stretchable Microelectrode Array (isMEA) for Neural and Muscular Surface Interfacing", IEEE Transactions on Biomedical Circuits and Systems, Feb. 2013, vol. 7, No. 1, pp. 1-10 <DOI:10.1109/TBCAS.2012.2192932>.
Harris, J. et al., "Mechanically adaptive intracortical implants improve the proximity of neuronal cell bodies", Journal of Neural Engineering, Nov. 2011, vol. 8, article 066011, 13 pages <DOI:10.1088/1741-2560/8/6/066011>.
Hassler, C. et al., "Polymers for Neural Implants", Journal of Polymer Science Part B: Polymer Physics, 2011 (available online Nov. 2010), vol. 49, No. 1, pp. 18-33 <DOI:10.1002/polb.22169>.
Hirsch, S. et al., "MR elastography of the liver and the spleen using a piezoelectric driver, single-shot wave-field acquisition, and multifrequency dual parameter reconstruction", Magnetic Resonance in Medicine, 2014 (available online Feb. 2013), vol. 71, No. 1 pp. 267-277 <DOI:10.1002/mrm.24674>.
Jackson, N. et al., "Long-term neural recordings using MEMS based movable microelectrodes in the brain", Frontiers in Neuroengineering, Jun. 2010, vol. 3, article 10, 13 pages <DOI:10.3389/fneng.2010.00010>.
Jeong, J-W. et al., "Soft Materials in Neuroengineering for Hard Problems in Neuroscience", Neuron, Apr. 2015, vol. 86, No. 1, pp. 175-186 <DOI:10.1016/j.neuron.2014.12.035>.
Karumbaiah, L. et al., "Relationship between intracortical electrode design and chronic recording function", Biomaterials, Nov. 2013 (available online Jul. 2013), vol. 34, No. 33, pp. 8061-8074 <DOI:10.1016/j.biomaterials.2013.07.016>.
Karumbaiah, L. et al., "The upregulation of specific interleukin (IL) receptor antagonists and paradoxical enhancement of neuronal apoptosis due to electrode induced strain and brain micromotion", Biomaterials, Sep. 2012, vol. 33, No. 26, pp. 5983-5996 <DOI:10.1016/j.biomaterials.2012.05.021>.
Khraiche, M. et al., "Early onset of electrical activity in developing neurons cultured on carbon nanotube immobilized microelectrodes", Annual International Conference of the IEEE Engineering in Medicine and Biology Society (Minneapolis, MN, Sep. 3-6, 2009), 2009 (Date added to IEEE Xplore: Nov. 2009), pp. 777-780.
Kim, D-H. et al., "Conducting polymers on hydrogel-coated neural electrode provide sensitive neural recordings in auditory cortex", Acta Biomaterialia, Jan. 2010, vol. 6, No. 1, pp. 57-62 <DOI:10.1016/j.actbio.2009.07.034>.
Kim, J. et al., "The mechanism of hydrophobic recovery of polydimethylsiloxane elastomers exposed to partial electrical discharges", Journal of Colloid and Interface Science, Dec. 2001, vol. 244, No. 1, pp. 200-207 <DOI:10.1006/jcis.2001.7909>.
Kolarcik, C. et al., "Elastomeric and soft conducting microwires for implantable neural interfaces", Soft Matter, Jun. 2015, vol. 11, No. 24, pp. 4847-4861 <DOI:10.1039/c5sm00174a>.
Kozai, T. et al., "Brain tissue responses to neural implants impact signal sensitivity and intervention strategies", ACS Chemical Neuroscience, Dec. 2014, vol. 6, No. 1, pp. 48-67 <DOI:10.1021/cn500256e>.
Kozai, T. et al., "Mechanical failure modes of chronically implanted planar silicon-based neural probes for laminar recording", Biomaterials, Jan. 2015 (available online Oct. 2014), vol. 37, pp. 25-39 <DOI:10.1016/j.biomaterials.2014.10.040>.
Kozai, T. et al., "Ultrasmall implantable composite microelectrodes with bioactive surfaces for chronic neural interfaces", Nature Materials, Nov. 2012, vol. 11, pp. 1065-1073 <DOI:10.1038/nmat3468>.
Lee, J. et al., "Palpation Device for the Identification of Kidney and Bladder Cancer: A Pilot Study", Yonsei Medical Journal, Sep. 2011, vol. 52, No. 5, pp. 768-772 <DOI:10.3349/ymj.2011.52.5.768>.
Lee, Y. et al., "Stretching-Induced Growth of PEDOT-Rich Cores: A New Mechanism for Strain-Dependent Resistivity Change in PEDOT:PSS Films", Advanced Functional Materials, 2013, vol. 23, pp. 4020-4027 <DOI:10.1002/adfm.201203670>.
Lempka, S. et al., "In vivo impedance spectroscopy of deep brain stimulation electrodes", Journal of Neural Engineering, Jun. 2009, vol. 6, No. 4, article 046001, 11 pages <DOI:10.1088/1741-2560/6/4/046001>.
Levental, L. et al., "Soft biological materials and their impact on cell function", Soft Matter, 2007 (available online Oct. 2006), vol. 3, pp. 299-306 <DOI:10.1039/B610522J>.
Lu, Y. et al., "Poly(vinyl alcohol)/poly(acrylic acid) hydrogel coatings for improving electrode-neural tissue interface", Biomaterials, Sep. 2009, vol. 30, No. 25, pp. 4143-4151 <DOI:10.1016/j.biomaterials.2009.04.030>.
Ludwig, K. et al., "Poly(3,4-ethylenedioxythiophene) (PEDOT) polymer coatings facilitate smaller neural recording electrodes", Journal of Neural Engineering, Jan. 2011, vol. 8, No. 1, article 014001, 7 pages <DOI:10.1088/1741-2560/8/1/014001>.
Manivasagam, G. et al., "Biomedical Implants: Corrosion and its Prevention—A Review", Recent Patents on Corrosion Science, 2010, vol. 2, pp. 40-54.
McClain, M. et al., "Highly-compliant, microcable neuroelectrodes fabricated from thin-film gold and PDMS", Biomedical Microdevices, Apr. 2011, vol. 13, No. 2, pp. 361-373 <DOI:10.1007/s10544-010-9505-3>.
Minev, L. et al., "Electronic dura mater for long-term multimodal neural interfaces", Science, Jan. 2015, vol. 347, No. 6218, pp. 159-163 <DOI:10.1126/science.1260318>.
Minev, L. et al., "Platinum-elastomer mesocomposite as neural electrode coating", APL Materials, Jan. 2015, vol. 3, article 014701, 5 pages <DOI:10.1063/1.4906502>.
Moxon, K. et al., "Long-Term Recordings of Multiple, Single-Neurons for Clinical Applications: The Emerging Role of the Bioactive Microelectrode", Materials (Basel), Dec. 2009, vol. 2, No. 4, pp. 1762-1794 <DOI:10.3390/ma2041762>.
Mueller, L. et al., "Liver stiffness: a novel parameter for the diagnosis of liver disease", Hepatic Medicine: Evidence and Research, 2010, vol. 2, No. 2, pp. 49-67 <DOI:10.2147/HMER.S7394>.
Muthuswamy, J. et al., "Adaptive neural interfaces for monitoring single neurons in the brain", Frontiers in Neuroscience, Sep. 2011, vol. 5, article 94, 11 pages <DOI:10.3389/fnins.2011.00094>.

(56) References Cited

OTHER PUBLICATIONS

Nguyen, J. et al., "Mechanically-compliant intracortical implants reduce the neuroinflammatory response", Journal of Neural Engineering, Aug. 2014, vol. 11, article 056014, 15 pages <DOI:10.1088/1741-2560/11/5/056014>.

Noh, H-S. et al., "Wafer bonding using microwave heating of parylene intermediate layers", Journal of Micromechanics and Microengineering, Feb. 2004, vol. 14, pp. 625-631 <DOI:10.1088/0960-1317/14/4/025>.

Patel, P. et al., "Insertion of linear 8.4µm diameter 16 channel carbon fiber electrode arrays for single unit recordings", Journal of Neural Engineering, Aug. 2015, vol. 12, article 046009, 18 pages <DOI:10.1088/1741-2560/12/4/046009>.

Patent Cooperation Treaty, International Searching Authority, International Preliminary Report on Patentability and Written Opinion for PCT/US2017/045470, 10 pages, report dated Aug. 4, 2017, opinion dated Nov. 21, 2017.

Patent Cooperation Treaty, International Searching Authority, International Search Report for PCT/US2017/045470, 4 pages, dated Nov. 21, 2017.

Polanco, M. et al., "Micromotion-induced dynamic effects from a neural probe and brain tissue interface", Journal of Micro/Nanolithography, Mems, and Moems, Jun. 2014, vol. 13, No. 2, article 023009, 7 pages <DOI:10.1117/1.JMM.13.2.023009>.

Polikov, V. et al., "Response of brain tissue to chronically implanted neural electrodes", Journal of Neuroscience Methods, Oct. 2005, vol. 148, No. 1, pp. 1-18 <DOI:10.1016/j.jneumeth.2005.08.015>.

Potter-Baker, K. et al., "Implication of chronic daily anti-oxidant administration on the inflammatory response to intracortical microelectrodes", Journal of Neural Engineering, May 2015, vol. 12, article 046002, 15 pages <DOI:10.1088/1741-2560/12/4/046002>.

Prasad, A. et al., "Abiotic-biotic characterization of Pt/It microelectrode arrays in chronic implants", Frontiers in Neuroengineering, Feb. 2014, vol. 7, article 2, 15 pages <DOI:10.3389/fneng.2014.00002>.

Prasad, A. et al., "Comprehensive characterization and failure modes of tungsten microwire arrays in chronic neural implants", Journal of Neural Engineering, Sep. 2012, vol. 9, article 056015, 21 pages <DOI:10.1088/1741-2560/9/5/056015>.

International Search Report and Written Opinion dated Nov. 21, 2017 in International Application No. PCT/US2017/045470.

\* cited by examiner

ULTRA-SOFT COATINGS FOR INTERFACES WITH BRAIN AND OTHER SOFT TISSUES

CROSS-REFERENCE

This patent application is a § 371 nationalization of International Application No. PCT/US2017/045470 filed Aug. 4, 2017, which claims priority to U.S. Provisional Application No. 62/370,836 filed Aug. 4, 2016, which applications are incorporated herein by specific reference in their entirety.

GOVERNMENT RIGHTS

This invention was made with government support under F32 NS073422 awarded by The National Institutes of Health. The government has certain rights in the invention.

BACKGROUND

Microfabricated neural implants and probes have revolutionized neural interface technologies by miniaturizing form factor and by increasing precision and functionality. However, a significant issue is long-term signal reliability wherein chronic recordings from neural probes tend to fail within a few weeks to several months after implantation. Dramatic changes in electrical characteristics of various implanted microarrays (tungsten, platinum-iridium), such as electrode impedance with large fluctuations in signal-to-noise ratios and recorded neural activity, have been shown up to 21 weeks in rats. Key biological failure modes may be attributed to loss of neurons near the electrode listening sphere and foreign body related inflammation and glial scarring.

Therefore, it would be advantageous to have improved microfabricated neural implants that have long term stability and consistent performance.

SUMMARY

In one embodiment, a soft conductive composite composition can include: a crosslinked silicone composition; and single-walled or multi-walled carbon nanotubes in the silicone composition.

In one embodiment, a soft conductive neural probe can include: a neural probe; and a soft conductive composition coating at least a portion of an implantable end of the neural probe, the soft conductive composition comprising a cross-linked silicone composition containing a plurality of single-walled or multi-walled carbon nanotubes.

In one embodiment, a method of making an implant can include: selecting PDMS precursors; cross-linking the PDMS precursor to obtain an elastic modulus of about 3-9 kPa or +/−1%, 5%, 10%, 20%, or 50%; selecting the carbon nanotubes; introducing the carbon nanotubes into the cross-linked PDMS to form a soft conductive composite composition; and coating the soft conductive composite composition onto at least a portion of an implant.

In one embodiment, a method of measuring properties at a neural interface can include: providing a neural probe having a soft conductive composition, the soft conductive composition comprising a cross-linked silicone composition containing a plurality of single-walled or multi-walled carbon nanotubes; implanting the neural probe having the soft conductive composition at a neural interface; and measuring a property with the neural probe.

In one embodiment, an implant for a tissue can include: an implant having a surface, and a crosslinked silicone composition on the surface and having a first elastic modulus adapted to be implanted into a tissue having the first elastic modulus or +/−1%, 5%, 10%, 20%, or 50% thereof, wherein the degree first elastic modulus is determined by a ratio of crosslinker and base.

In one embodiment, a method of making a tissue compatible implantable composition can include: selecting a tissue to receive the implant; determining an elastic modulus of the tissue; selecting PDMS precursors; and cross-linking the PDMS precursor to obtain the elastic modulus of the tissue or +/−1%, 5%, 10%, 20%, or 50% to obtain the tissue compatible implantable composition.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
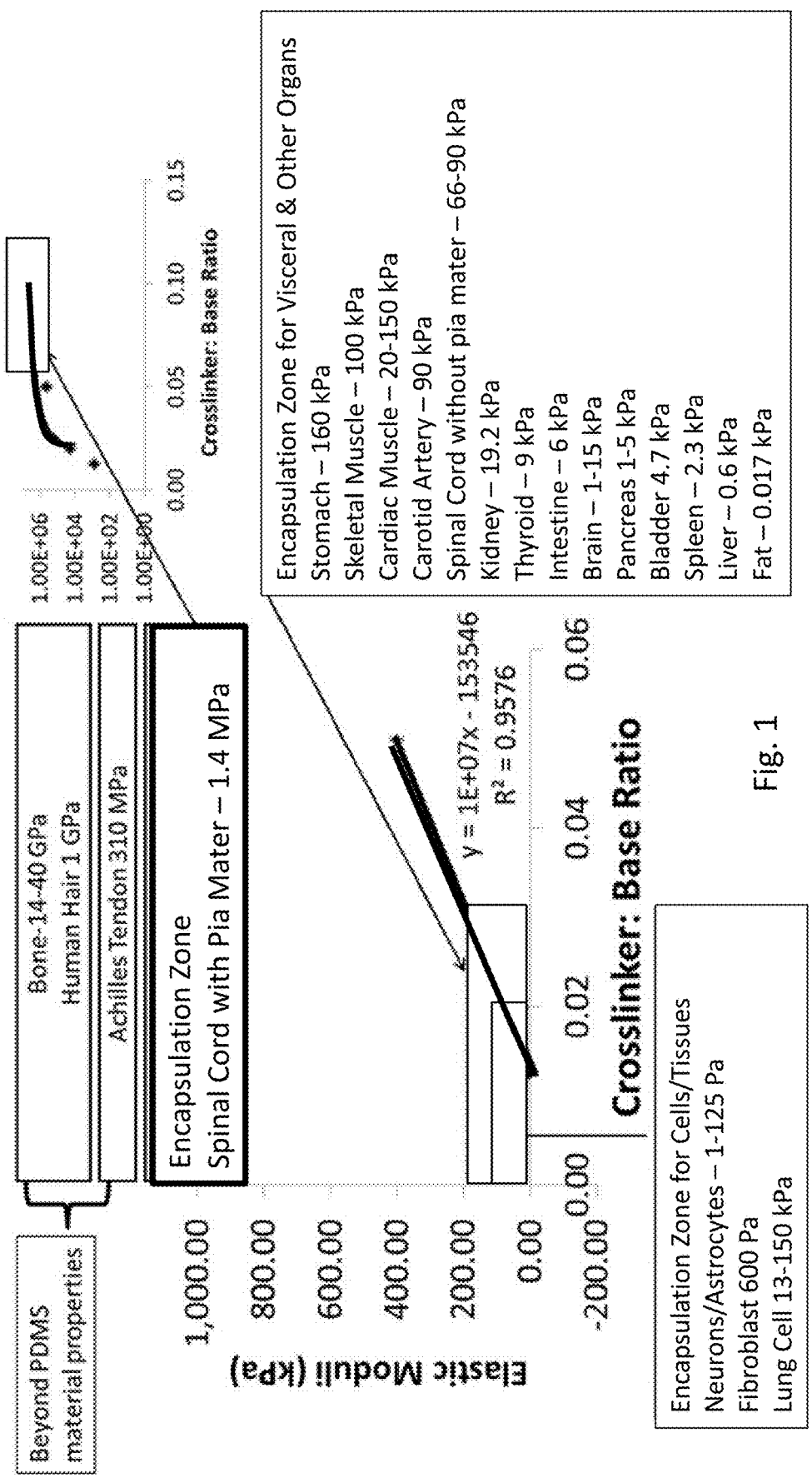
FIG. 1 shows graphs of elastic moduli versus the crosslinker to base ratio along with the elastic moduli of various tissues so that the crosslinker to base ratio can be selected to prepare a soft conductive material with the same elastic modulus as a tissue that will receive the implant having the crosslinked material.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes biocompatible materials that provide a soft interface material that can be implanted as an implant or coated onto a harder material for an implant. The interface material can include viscoelastic properties that match that of an organ or tissue, such as brain tissue. The biocompatible material can include conductive elements, such as particles or other structures (e.g., carbon nanotubes) that can function at neural interfaces, and improve the long-term, electrical performance of an electrode implant at the neural interface.

In one embodiment, the material has an elastic modulus that is brain-like, there by the material provides a soft elastomeric interface with an elastic modulus of ~5-8 kPa and has a time-constant of relaxation after a step-indentation that is closely matched with the visco-elastic properties of the brain. This allows the material to be used at an interface of a tissue and an implant. The elastomeric material with brain-like mechanical properties can be prepared as composites of PDMS derivatives having conductive elements, such as single-wall carbon nanotubes (SWNTs) and multi-walled nanotubes (MWNTs) or any carbon nanotubes. The electrical performance of implants coated with the conductive elastomeric material shows good electro-chemical impedance spectra.

Mechanically-matched biocompatible coatings can improve long-term biocompatibility on biomedical implants. Currently, biomedical implants are made of materials with high elastic moduli in contrast to the elastic module of biological tissue and organs. The mechanical mismatch between biomaterial and implant often leads to long-term failure as well characterized in bone/hip implants/orthopedic applications.

In one embodiment, probes can be implanted. As such, interfaces of probes and tissue can be prepared so that mechanically the probe has an elastic modulus that matches the tissue. It has been found that correcting mechanical matching can be useful for implants that are implanted into soft tissues, such as the brain. The mechanical matching can be useful for numerous implants for different visceral organs and ultra-soft biological systems by matching the elastic moduli of organs to a tunable, silicone material. Silicone based materials better emulate the mechanical properties of biological systems by their viscoelastic and general elastic moduli parameters.

Now, implants can include a correct mechanical match between cortical implants and the brain via a silicone based material. Materials between $10^0$ Pa to $10^3$ Pa can include polyacrylamine, dextran, gelatin, agarose, hyaluronic acid, or others. Materials between $10^2$ Pa to $10^6$ Pa can include polyethylene glycol (PEG), crosslinked gelatin, methylcellulose, or others. Materials between $10^5$ Pa to $10^9$ Pa can include Teflon (e.g., tetrafluoroethylene, PTFE), polyamidoamine (PAMAM) dendrimer, polyvinylacetate, polyvinylacetate/cellulose, rubbers, polydimethylsiloxane (PDMS), or others. Materials between $10^9$ Pa to $10^{10}$ Pa can include parylene-C, polymethylmethacrylate (PMMA), polyvinylfluoride films, polyimide, polystyrene, polyethylene terephthalate (PET), or others. Materials between $10^{10}$ Pa to $10^{12}$ Pa can include carbon nanotubes, tungsten, stainless steel, polysilicon, or others. It should be noted that a single neuron is between about $10^1$ Pa to $10^2$ Pa, which can allow for selection of a proper material. It should be noted that a single astrocyte is between about $10^2$ Pa to $10^3$ Pa, which can allow for selection of a proper material. It should be noted that brain tissue is between about $10^3$ Pa to $10^4$ Pa, which can allow for selection of a proper material. It should be noted that a blood vessel is between about $10^5$ Pa to $10^6$ Pa, which can allow for selection of a proper material. It should be noted that dura mater is between about $10^7$ Pa to $10^8$ Pa, which can allow for selection of a proper material. It should be noted that bone is between about $10^9$ Pa to $10^{10}$ Pa, which can allow for selection of a proper material. It should be noted that tissue scaffolds are between about $10^0$ Pa to $10^7$ Pa, which can allow for selection of a proper material. It should be noted that insulation material can be between about $10^6$ Pa to $10^7$ Pa, which can allow for selection of a proper material. It should be noted that electrodes are between about $10^{10}$ Pa to $10^{13}$ Pa, which can allow for selection of a proper material. Accordingly, the location of the implant and biomaterial that will be associated with the implant can be used to determine the material that is used as an outside material of an implant.

Additionally, FIG. 1 provides graphs of the elastic moduli (kPa) versus the crosslinker:base ratio to make suitable materials for specific biological materials, which are identified and correlated with the graphs. The graphs can be used to determine the material and the crosslinker:base ratio to make a material compatible for a particular tissue. Particularly, the invention can use the versatile and tunable capabilities of the polydimethyl siloxane (PDMS) in accordance with FIG. 1. Please note that PDMS as a USP Class VI material. PDMS may be fabricated using alternate chemical precursors including Sylgard 184 (as used here for testing the concept). Other USP Class VI based precursor materials include Dow Corning MDX4-4210, which has been classified as a medical grade material for PDMS and is similar in surface chemistry to Sylard 184. Using Sylgard 184, the base (e.g., PDMS precursor) to crosslinker ratio was varied to generate different elastic moduli. The values for elastic moduli were measured using an indentation method using a stainless-steel, spherical indentor (e.g., 4 mm) diameter. Using Hertzian model, the elastic moduli were estimated using the following standard equation (Equation 1) for spherical indentors.

$$F=(4/3)(E/1-v^2)(\sqrt{R})(\delta^{(3/2)})$$ Equation 1

In Equation 1, F is the measured force, E is the elastic modulus, v is the Poisson's ratio assumed to be 0.5 for silicone based elastomeric materials, R is the radius of the indentor, and δ represents the indentation depth.

The spherical indentor was used to indent 200 μm into the silicone gel. As seen in FIG. 1, the change in crosslinker:base ratio modulates the elastic moduli in a non-linear manner (upper right on diagram). The majority of the mechanical properties of soft organs and tissues fall within 0-200 kPa range for elastic moduli. The PDMS material can be tuned to match the elastic moduli of these visceral organs using the presented calibration curve in this fairly linear region.

PDMS by itself has strong protein adhesion characteristics, which may be favorable in some instances. In other instances, the surface of the soft conductive composition can be modified to have less adhesion with proteins, such as by passivation or making it hydrophilic or coating with a hydrophilic coating (e.g., PEG). The PDMS surface chemistry is highly conducive to strategies that may prevent protein adsorption, such as prevention of hydrophobic recovery using presoaking conditions (e.g., presoaking in aCSF for 24 hours) and other surface chemical modifications. Surface chemical modification strategies we have proposed include; hydrosilanization treatment of PDMS surfaces with DC1107 (Dow Corning) and 2% triflic acid in methanol for Si—H surface functionalization and subsequent hydrosilylation reaction by refluxing the substrate in a solution with equal parts of diethylene glycol dimethylether and poly (ethylene glycol) monoallylether (allyl-PEO-OH) with Karstedt's Pt catalyst for 2 hours. The PEO/PEG groups will prevent non-specific protein adhesion. PEO/PEG linkages for increased hydrophilicity. Functionalization for specific applications (e.g., with selective peptides) is also a possibility.

A method for preparing a conductive silicone composite for any degree of elastic modulus (e.g., softness) can be used for preparing the implants of the invention that are matched with a specific organ or tissue for matching mechanical properties. In step 1, the silicone precursor base, crosslinker, and conductive implant material (e.g., functionalized carbon nanotubes) are provided. In step 2, the silicone precursor base is reacted with the crosslinker (e.g., vinyl crosslinker) in a manner where the ratio of crosslinker:base is determined from data, such as FIG. 2 in order obtain the desired elastic modulus for the silicone composite, where the silicone precursor base and crosslinker are pre-mixed (e.g., about 5 minutes). In step 3, the silicone precursor base and crosslinker mixture are combined with the conductive implant material and mixed vigorously for about 5 minutes to about 15 minutes by standard mixing (e.g., any type of mixing) or gentle sonication. In step 3, the conductivity of the resulting implant can be controlled by controlling the amount of conductive implant material (e.g., controlling amount of functionalized carbon nanotubes). The conductive implant material (e.g., carbon nanotube-COOH) can be suspended in a solvent, such as toluene, TMF, or DMSO, to disperse bundles for higher conductivity prior to mixing with the silicone precursor base and crosslinker. For about 1 mg conductive implant material per 500 mg (base), about 30-40 kohms*cm resistivity can be about 0.2% w/w, which can be modulated to obtain the desired modulus and conductivity, such as up to 5% w/w without significant change of the elastic modulus. In step 4, the mixture is no longer mixed and allowed to rest for about 15 minutes to 2 hours at room temperature in a vacuum chamber, which can remove bubbles and allow for better equal dispersion of the carbon nanotubes and/or crosslinker into the elastomer matrix. In step 5, the mixture is then heated to 60-80 degrees C. for up to 18 hours or more. In one aspect, step 5 can use thermal induction of polymerization. At room temperature it can take about 60 hours to achieve the same modulus. At a higher temperature of about 120 degrees C. it can be about 1 hour for 1-3 g small batches. Also, UV/photocurable crosslinkers can be used with the carbon nanotubes incorporated in the matrix. In step 6, the crosslinked polymer is placed into a solution with similar osmolarity plus salt balance compared to an organ of interest (e.g., brain artificial cerebrospinal fluid) for at least 12 hours, or at least 24 hours, or where this solution is used for storage of the crosslinked polymer. Optionally, a step to passivate the surface of the crosslinked polymer can be performed to render it hydrophilic (without using O2 plasma). Chemical addition of PEG or other hydrophilic polymer can be optional. Also, optionally, the surface of the polymer can be made conductive to electron transport under aqueous conditions. Another option is to remove unreacted vinyl or other unreacted reagents.

Figure 2:
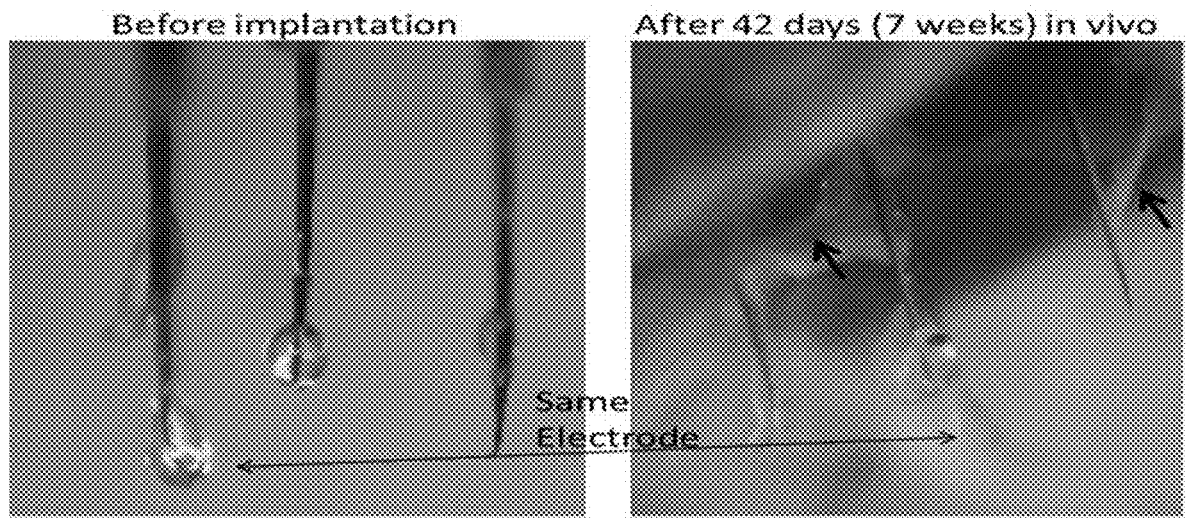
FIG. 2 shows images of an electrode implant having the soft conducive material described herein before and after implantation.

FIG. 2 shows results of an experiment using the soft conductive composition on electrodes, with pictures showing before implantation and after 7 weeks of implantation in vivo. This shows that the soft conductive brain-matched silicone composite after 7 weeks of implantation shows negligible tissue adhesion or growth, in addition to maintaining mechanical integrity. Arrows show the tissue adhesion in uncoated areas.

It has been found that the soft conductive composition can also be used for interfaces between implants and other tissues. That is, the implant includes the soft conductive composition on a surface that interfaces with a tissue. As such, the tissue can be selected, and the elastic modulus of the tissue can be identified. The soft conductive composition can then be prepared with selective crosslinking to obtain about the elastic modulus of the tissue. The selective crosslinking can be obtained by using the graph that shows the obtained elastic modulus for the ratio of crosslinker to base (e.g., PDMS precursor or reagent). The carbon nanotubes can then be added, such as the amounts described herein, when for use in conductivity or on a conductive interface. The carbon nanotubes can be minimal when not used as a conductive interface. The soft conductive composition can then be coated on a medical device (e.g., implantable medical device) or other implant. The coating can be onto a polymeric, ceramic, or metal surface. The soft conductive composition can then be processed, such as passivation or otherwise making hydrophilic), before implantation.

Potential applications of the soft conductive composition include any of the following, with the elastic modulus being matched to the tissue into or onto which the implant is implanted: artificial tissue implants as coating or matrix; implantable microfluidics as coating on microfluidics; inert coatings for implantable micro-devices such as glucose sensors, insulin pumps, etc.; 'smart' interfaces (e.g., coatings) for implantable bioelectronics (i.e. PCBs, microchips)

using PDMS/Nanotube interface; coatings or matrix for artificial organs (e.g., via 3D Bioprinting); encapsulation of small populations of genetically modified cell/tissues; or coating of catheters or other similar device.

As recited herein, the elastic modulus can be modulated by modulating the degree of crosslinking. As such, modulating the degree of crosslinking can be performed by modulating the ratio of crosslinker to base ratio. Here, the crosslinker is the chemical that causes crosslinking to occur, such as crosslinking the molecules of the base. Here, the base is the chemical that is being crosslinked, such as the reagent that is crosslinked into PDMS. Table 1 shows the changes of elastic modulus by modulating the crosslinker to base ratio.

TABLE 1

Effect of crosslinker to base ratios of PDMS/functionalized carbon nanotube composite on elastic modulus

| Crosslinker to Base Ratio | Elastic Modulus (kPa) |
|---|---|
| 0.1 (1:10) | 846 |
| 0.05 (1:20) | 40 |
| 0.025 (1:40) | 16.3 |
| 0.020 (1:50) | 17.9 |
| 0.0125 (1:80) | 0.756 |

The reported elastic modulus for PDMS/carbon nanotube composite is lower than that for PDMS alone. For instance, an example composite is approximately 3 times softer compared to elastic modulus values (2.6 MPa) for 1:10 ratio for PDMS (Sylgard 184). In fact, the example having 1:10 crosslinker:base composite is much closer to the literature equivalent PDMS values of 1:25.

It is surprising and unexpected that the incorporation of the functionalized carbon nanotube into the elastomer matrix contributed to this effect.

Literature reports of composites with carbon nanotube fillers in PDMS show increasing trends in elastic modulus and impose increasing material strength compared to polymer alone (i.e. >200% increase in elastic modulus for 2% carbon nanotube weight). Therefore, the inventive soft interfaces described herein have counterintuitive trends in elastic material properties with incorporation of functionalized carbon nanotubes.

Figure 3:
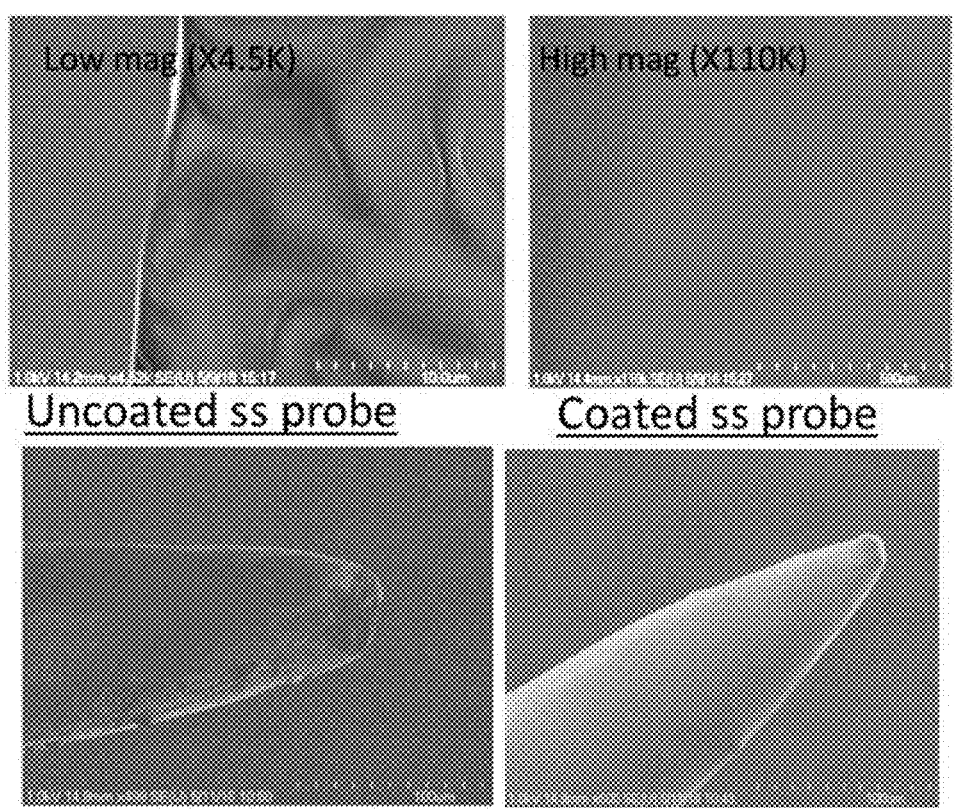
FIG. 3 shows images of an electrode implant with and without the soft conductive material described herein.

Comparing morphology with a 0.5% carbon nanotube filler, nanotube bundles are far apart but still visible. The present inventive composite material shows smooth morphology (see FIG. 3) with no protruding carbon nanotubes at 0.25% suggesting incorporation of the carbon nanotube into the elastomer network chemical structure. FIG. 3 shows FESEM images of brain-matched silicone/CNT composite on a silicon wafer at: 4.5K magnification, and 110K magnification showing a smooth surface with no protrusions or obvious texture. The bottom left image shows an uncoated stainless-steel (ss) probe and the bottom right image shows a composite coated stainless-steel (ss) probe. The coating removes apparent textures on the contacting surface to provide a smooth surface, which is compatible with tissues and favorable for an implant.

Figure 4:
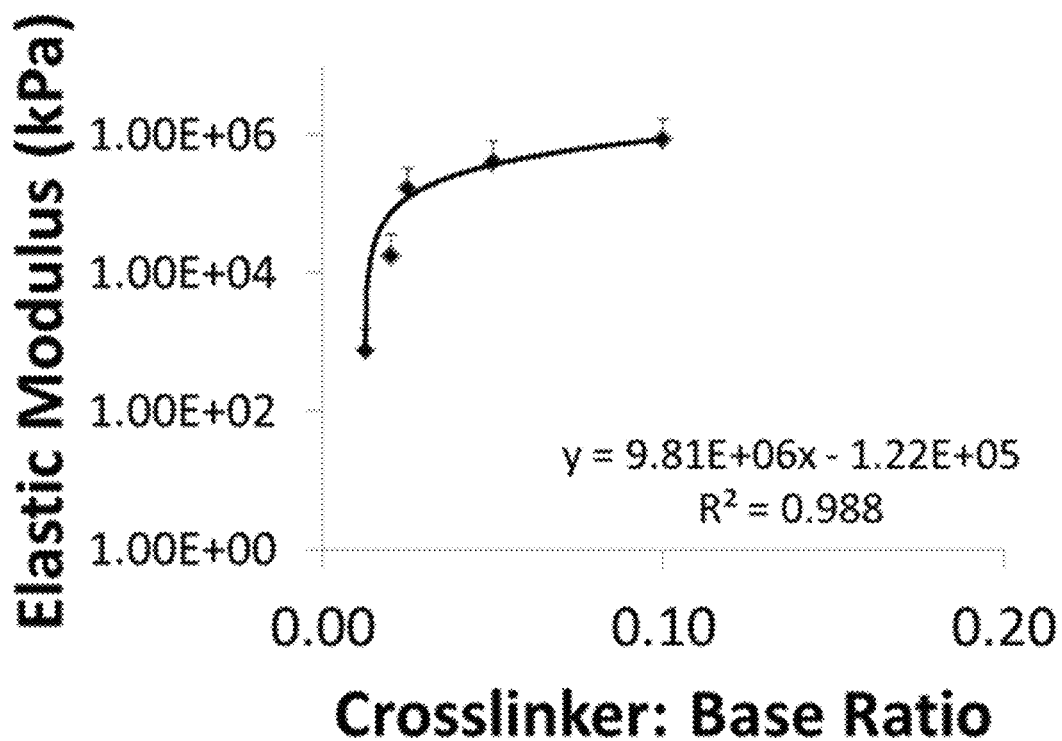
FIG. 4 shows an expanded graph of elastic moduli versus the crosslinker to base ratio for a soft conductive material.

For the experiments involving brain-matched coatings described herein, the experiments use a 0.0133 (1:75) crosslinker to base ratio with 0.2%-0.5% carbon nanotubes to achieve required impedance (~1 MOhm) for recording neural activity from single neurons. Using a regression-derived equation, a 5 kPa elastic modulus would therefore require a composition of 0.013 (1:77) crosslinker to base ratio (FIG. 4). FIG. 4 shows the crosslinker to base ratio modulation curve for PDMS/Nanotube composite.

In one embodiment, the crosslinker, silicone precursor base, and conductive carbon nanotubes can be prepared into a soft conductive composite composition. Such a soft conductive composite composition can include a crosslinked silicone composition, and single-walled or multi-walled carbon nanotubes in the silicone composition. In one aspect, the soft conductive composite can have an elastic modulus of about 4 kPa, 3 to 8 kPa, or 2 to 9 kPa, or +/−1%, 5%, 10%, 20%, or 50%. In one aspect, the soft conductive composite has an elastic modulus of about 5-8 kPa or +/−1%, 5%, 10%, 20%, or 50%. In one aspect, the soft conductive composition has an elastic modulus matched with brain tissue or other soft tissue of interest. In one aspect, the soft conductive composition is crosslinked with a vinyl crosslinker. In one aspect, the soft conductive composition includes Sylgard 184. In one aspect, the soft conductive composition includes the carbon nanotubes at less than 5% w/v. In one aspect, the soft conductive composition includes the carbon nanotubes at a range of about 0.2% to 1% w/v. In one aspect, crosslinking of the soft conductive composition is defined by the ratio of the crosslinker and base. In one aspect, the elastic modulus is y and the ratio of the crosslinker to base is x, and wherein $y=9.81E6*x-1.22E5$ (±20% variation). The carbon nanotubes can be present at about 1 mg per 500 mg (base): 30-40 kohms*cm resistivity)=0.2% w/w, but can go up to 5% w/w without significant change in elastic modulus.

In one aspect, the soft conductive composition is configured for electrical conductance by varying the amount of carbon nanotubes, with more (e.g., higher concentration) being more conductive and less (e.g., lower concentration) being less conductive. In one aspect, the soft conductive composition can be configured as an implant, such as for brain interface implantation, by having a matching elastic modulus. The soft conductive composition can be applied to an implantable medical device. The soft conductive composition can be configured to stabilize electro-chemical impedance and to stabilize neural recordings.

In one embodiment, the soft conductive composition can be applied to an implant, and may be an outer coating of a portion of the entirety of the implant. An example can include a neural probe coated with the soft conductive composition. The soft conductive composition is configured to be stable when implanted in order to maintain stable mechanical properties for at least 4 weeks, such as when on an implant. In one aspect, the soft conductive composition at least partially coats a conventional metal implant or doped semiconductor implant.

In one embodiment, the soft conductive composition includes a biological active agent, such as a drug. The drug can be therapeutic for a disease or to inhibit a biological process such as inflammation that can occur around an implant. In one example, the soft conductive composition can include an anti-inflammatory contained therein.

In one embodiment, the soft conductive composition has a biocompatible coating thereon. Often, the coating is softer than the soft conductive composition, and can be any biocompatible composition, such as a biocompatible polymer.

In one aspect, the soft conductive composition is a silicone composition, such as a PDMS silicone. The silicone composition can be a derivative of PDMS silicone. The silicone composition can be crosslinked. For example, the silicone composition is crosslinked by selecting an amount of crosslinking to arrive at the desired elastic moduli.

In one embodiment, the conductive material in the soft conductive composition is a carbon nanotube, which can be present at less than 5% or less than 1% w/v. The carbon nanotubes can include carboxylic acid functional groups. The carbon nanotubes can be included in 5 nm×500 nm bundles or individual nanotubes.

In one embodiment, an implant can include an insulation material (e.g., insulating rubber or polymer) between the harder implant body and soft conductive composition. On the other hand, the composition can be devoid of insulation between the implant and soft conductive composition. In one aspect, the implant is devoid of an insulation material between the implant body and soft conductive composition.

In one embodiment, the hard implant body can be a metal implant, such as a material that includes a metal selected from the group consisting of stainless steel, platinum, platinum-iridium, silver/silver-chloride, gold, and tungsten In one aspect, the soft conductive composition includes a relaxation time constant to match the relaxation time constant of brain or other soft tissue of interest.

In one embodiment, an implant can include a substrate with soft conductive composition thereof, whether partially or completely encapsulating the substrate or coated on an implantable portion, where a non-implantable portion may be devoid of the soft conductive composition. In one aspect, the substrate may be a neural probe. In one aspect, the implant may include: a neural probe; a soft conductive composition coating an implantable end of the neural probe, the soft conductive composition comprising a cross-linked silicone composition containing a plurality of single-walled or multi-walled carbon nanotubes. However, the substrate may be a sensor or sensor portion that is implanted or at least introduced into a biological fluid and/or introduced to contact soft tissue in a subject. The soft conductive composition may include any of the properties described herein, such as elastic modulus, electrical conductance, or the like. In one aspect, the substrate is configured as an implant, such as for brain interface implantation. In one aspect, the soft conductive composition has a desired degree of crosslinking that is obtained by a selected ratio of crosslinker to base.

In one aspect, the substrate is a neural probe or other sensor with electrical conductance. The soft conductive material can be configured to stabilize electro-chemical impedance over implant durations lasting more than 1 year. In one aspect, the sensor can be a neural probe and the soft conductive material is configured to stabilize neural recordings from the neural probe. In one aspect, an elongate portion of the neural probe or other sensor or implant can be coated with the soft conductive composition. In one aspect, the soft conductive composition at least partially coats a conventional metal implant or doped semiconductor implant.

In one embodiment, a method of making an implant or an implantable portion of a medical device, or other device is provided. In one example, the implant can include a neural probe. Such a method of making can include: selecting one or more PDMS precursors; cross-linking the PDMS precursor to obtain an elastic modulus of about 3-9 kPa or +/−1%, 5%, 10%, 20%, or 50%; selecting the conductive elements to be carbon nanotubes or other conductive elements; introducing the carbon nanotubes or other conductive elements into the crosslinked PDMS to form a soft conductive composite composition; and coating the soft conductive composite composition onto a neural probe. In one aspect, wherein the implant portion having the soft conductive composition includes metal implants or doped semiconductor implants.

In one aspect, the method can include degassing/de-bubbling the soft conductive composite composition. In one aspect, the method can include dry incubating the neural probes coated with the soft conductive composite composition. In one aspect, the dry incubating is at less than 5% humidity. In one aspect, the dry incubating is at a temperature of about 60 degrees C., or +/−1%, 5%, 10%, 20%, or 50%.

In one embodiment, the method can include curing the soft conductive composite composition onto the neural probe.

In one embodiment, the method can include testing the soft conductive composition assessing whether or not the soft conductive composite composition has a strong hysteresis.

In one embodiment, the method can include rinsing the implant (e.g., neural probe) having the soft conductive composition with deionized water.

In one embodiment, the method can include passivating the surface of the soft conductive composition. In one aspect, the method can include passivating the neural probe having the soft conductive composition with aCSF (7.4 g sodium chloride, 2.1 g sodium bicarbonate, 0.17 g sodium phosphate monobasic, 0.19 g magnesium chloride, 4.5 g glucose in filtered, 1 liter of deionized water). In one aspect, the method can include incubating the soft conductive composition in a fluid having similar osmolarity as brain. In one aspect, the method can include passivating the surface of the soft conductive composition for 24 hours.

In one embodiment, the method can include mechanically characterizing the neural probe having the soft conductive composition to have an elastic modulus of about 3-9 kPa or +/−1%, 5%, 10%, 20%, or 50%. In one aspect, the method can include assessing stability by incubating the neural probe having the soft conductive composition in aCSF (7.4 g sodium chloride, 2.1 g sodium bicarbonate, 0.17 g sodium phosphate monobasic, 0.19 g magnesium chloride, 4.5 g glucose in filtered, deionized water) for at least 1 week.

In one embodiment, the method can include controlling the degree of cross-linking the PDMS precursor to obtain the elastic modulus. In one aspect, the method can include using the tuning curve for elasticity versus ratio of crosslinker to base in order to tune the elastic moduli to match the elastic moduli of the cortical brain, and with an elastic modulus of approximately 5±3 kPa with shear modulus of 1.2-1.4 kPa.

In one embodiment, the method can include: obtaining a crosslinker to base curve for the crosslinker and base PDMS precursor; determining a desired elastic modulus;

determining an amount of crosslinker for an amount of base PDMS precursor; and crosslinking the base PDMS with the amount of crosslinker according to the curve to obtain the desired elastic modulus for the soft conductive composition.

In one embodiment, the method can include making the surface of the soft conductive composition hydrophilic. In one aspect, the method can include coating the surface of the soft conductive composition with a hydrophilic coating.

In one aspect, the method can include removing unreacted crosslinker from the soft conductive composition.

In one embodiment, a method of measuring properties at a neural interface can include: providing a neural probe having the soft conductive composition; implanting the neural probe having the soft conductive composition at a neural interface; and measuring a property with the neural probe. In one aspect, the method can include measuring stability of electro-chemical impedance. In one aspect, the method can include performing neural recordings. In one aspect, the method can include incising dura for implantation of the neural probe. In one aspect, the method can include placing gelfoam over the neural probe after implantation. In one aspect, the method can include implanting into a neural interface of the brain. In one aspect, the method can include securing the neural probe onto the skull. In one aspect, the method can include securing the neural probe onto the skull with dental cement (PMMA). In one aspect, the method can include performing electrochemical impedance spectroscopy with the neural probe. In one aspect, the method can include performing neural recordings with the neural probe.

In one embodiment, an implant for a tissue can include: an implant having a surface, and a crosslinked silicone composition on the surface and having a first elastic modulus adapted to be implanted into a tissue having the first elastic modulus or +/−1%, 5%, 10%, 20%, or 50% thereof, wherein the degree first elastic modulus is determined by a ratio of crosslinker and base (e.g., silicone reagent). In one aspect, the surface is polymeric, ceramic, or metal.

In one embodiment, a method of making a tissue compatible implantable composition can include: selecting a tissue to receive the implant; determining an elastic modulus of the tissue; selecting PDMS precursors; and cross-linking the PDMS precursor to obtain the elastic modulus of the tissue or +/−1%, 5%, 10%, 20%, or 50% to obtain the tissue compatible implantable composition. In one aspect, the method can include determining a ratio of crosslinker and PDMS precursor to obtain crosslinking that results in the elastic modulus. In one aspect, the method can include selecting the carbon nanotubes, and introducing the carbon nanotubes into the crosslinked PDMS to form a soft conductive composite composition. In one aspect, coating the tissue compatible implantable composition onto an implantable medical device.

Figure 10A:
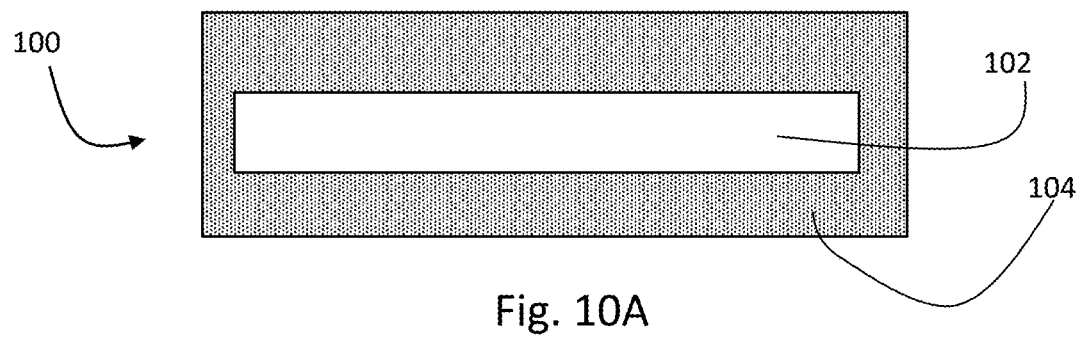
FIG. 10A shows a schematic representation of an implant 100 having an implant substrate 102 and a soft conductive material 104 encapsulating the implant 100.

FIG. 10A shows a schematic representation of an implant 100 having an implant substrate 102 and a soft conductive material 104 encapsulating the implant 100.

Figure 10B:
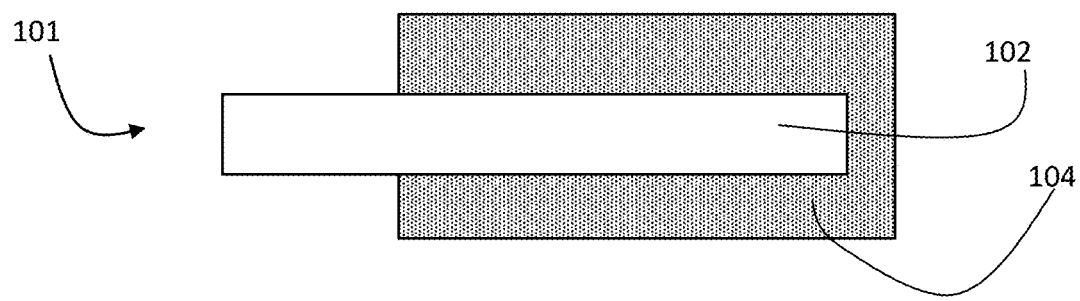
FIG. 10B shows a schematic representation of an implant 101 having an implant substrate 102 and a soft conductive material 104 partially encapsulating the implant 100.

FIG. 10B shows a schematic representation of an implant 101 having an implant substrate 102 and a soft conductive material 104 partially encapsulating the implant 101.

Figure 10C:
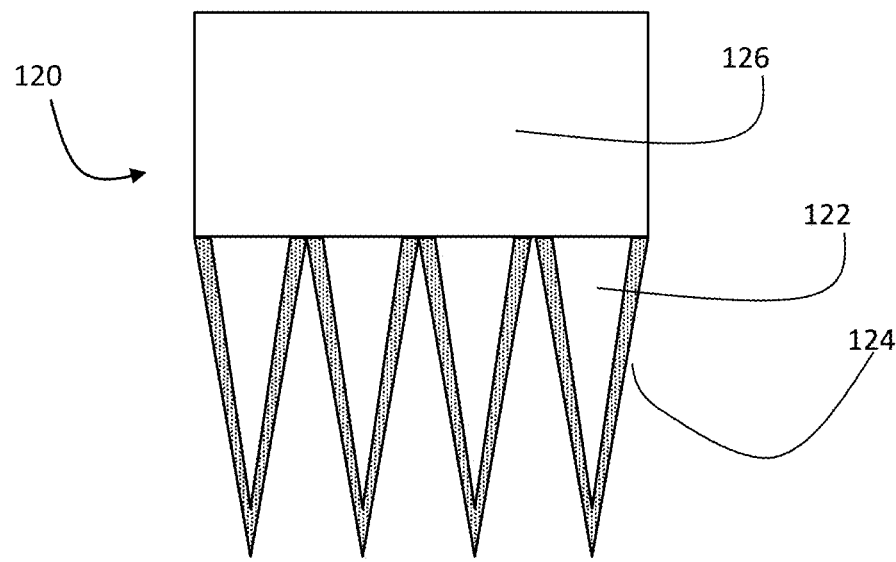
FIG. 10C shows a schematic representation of a device 120 having a plurality of implantable substrates 122 and a soft conductive material 124 covering the implantable portion of implantable substrates 122, and a non-implantable portion 126 devoid of the soft conducive material.

FIG. 10C shows a schematic representation of a device 120 having a plurality of implantable substrates 122 and a soft conductive material 124 covering the implantable portion of implantable substrates 122, and a non-implantable portion 126 devoid of the soft conducive material.

The soft materials can improve the biocompatibility of neural interface devices by reducing glial scarring and associated immune reactions. In addition, the soft material can reduce interfacial, mechanical strain at implant sites. The soft interfacial material can be configured to be brain-like in its mechanical properties and assess the stability of electro-chemical impedance at the interface. Suitable exemplary implants can include neural probes coated with the soft material. A soft and conductive composite (~5 kPa elastic modulus) can include silicone derivatives and single-walled or multi-walled carbon nanotubes for conductivity. Tungsten microelectrodes can be coated with the soft silicone composite. Also, Pt/Ir microelectrodes can be coated with soft silicone composite were implanted in 6 animals for durations ranging from 5 weeks to over 1 year. Electrochemical impedance spectroscopy was used to assess the quality of the brain-tissue-electrode interface under chronic conditions. Neural recordings were assessed for unit activity, signal-to-noise ratio (SNR), and noise levels for over 1 year of implantation in rodents.

In vitro studies provided herein showed that the soft, silicone materials maintained stable elastic modulus and mechanical properties over 4 weeks. Primary neurons cultured on the soft material showed increased viability and branching. Electrodes with soft conductive silicone coatings showed relatively stable electrical impedance characteristics and noise levels over durations ranging from 5 weeks to over 1 year compared to the uncoated control electrodes.

The silicone based materials incorporated with CNTs can be tuned to an elastic modulus of ~5 kPa, similar to rat cortical brain, by varying the levels of cross-linking (FIG. 1). Under small strains, both the brain tissue (FIG. 5A) and the silicone/CNT composite (FIG. 5B) reported here resemble a Maxwell type model with time constants for stress relaxation that correspond to a fast phase followed by a slow phase. In this current study, viscoelastic relaxation properties of brain tissue were matched by tuning the fast relaxation phase of the soft, silicone composite to match that of brain tissue. A step indentation methodology was utilized to measure and match the viscoelastic properties of in vivo cortical tissue and silicone/composite materials (see methods). As shown in FIG. 5C, the median time constant for the fast relaxation phase of the brain tissue (13.3 sec) closely matched the soft silicone composite (17.2 sec). Both of the above time-constants were significantly larger than the median time constant of 0.5% agarose gel (5.99 sec) that is commonly used as a model of brain tissue. Longer relaxation time constants imply lower strains and strain rates, potentially leading to reduced micromotion induced long-term injury. Accordingly, the soft, brain-like silicone/CNT based composites descried herein are excellent candidates for mimicking the viscoelastic properties of cortical brain tissue.

Force-displacement curves for in vivo rat cortical brain data (FIG. 5A) and soft, brain-like composites (FIG. 5B) and 0.5% agarose hydrogel using a stainless-steel conical probe with 5° taper at 10 μm/sec penetration speed are shown. Arrows indicate the instant when electrode movement was stopped after reaching a depth of 1 mm, beyond which the forces relax due to viscoelastic relaxation of material against the electrode. FIG. 5C shows the viscoelastic material properties characterized by a second order prony series model were used to determine the relaxation properties of rat cortical brain, soft, brain-like composites and 0.5% agarose hydrogel (commonly used brain phantom). Tukey box-plots of short-term relaxation time constants show the median short-term relaxation time constants for brain tissue (13.3 sec), for soft brain-like composite (17.2 sec) and for 0.5% agarose hydrogel (5.99 sec). The short-term relaxation time-constants of cortical brain and soft silicone composite were not significantly different. Comparison of force-displacement curves during the initial penetration of 200 μm between soft brain-like composites in FIG. 5D and rat cortical brain tissue in FIG. 5E. Force-displacement curves were generated using a stainless-steel conical probe driven at 10 μm/sec using an FHC Microdrive (Bowdoin, Me.).

Figure 4A:
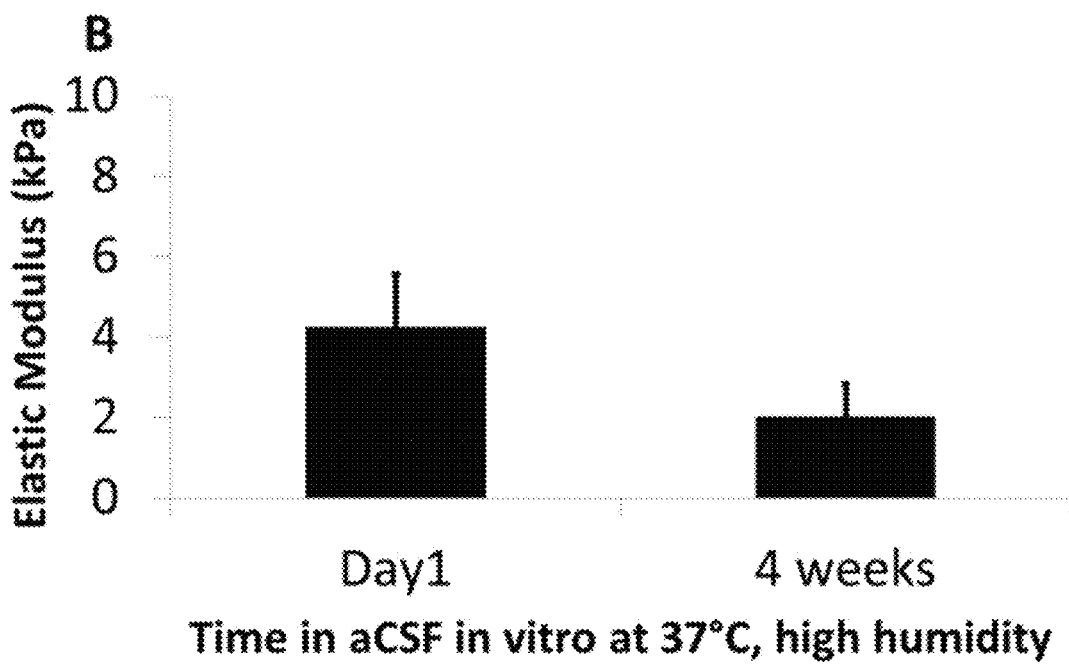
FIG. 4A shows a graph of the elastic modulus for a passivated soft conductive material at day 1 and 4 weeks.
Figure 6B:
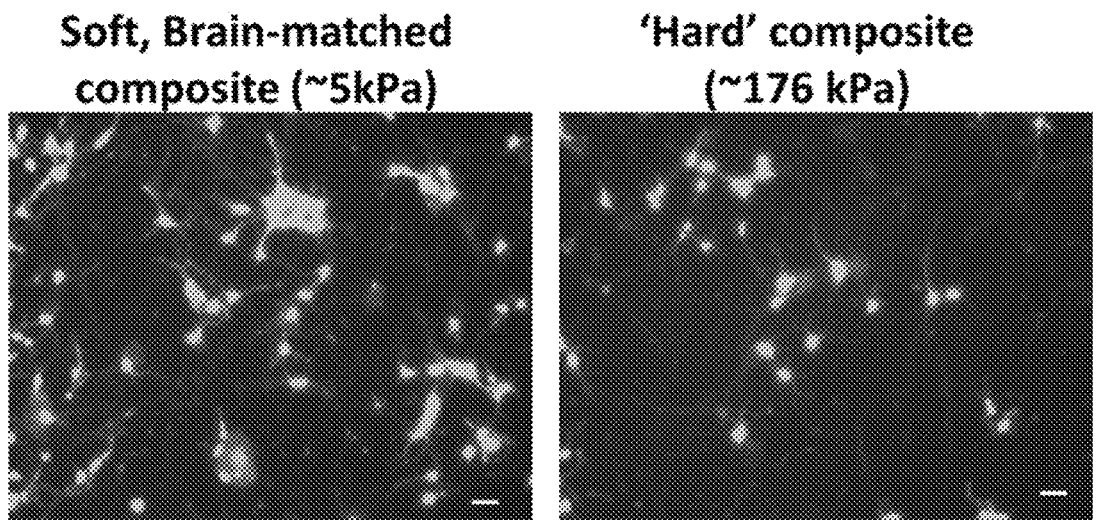
FIG. 6B shows images of cortical neuron growth on the softer conductive composite (left) and for a hard composite).
Figure 6A:
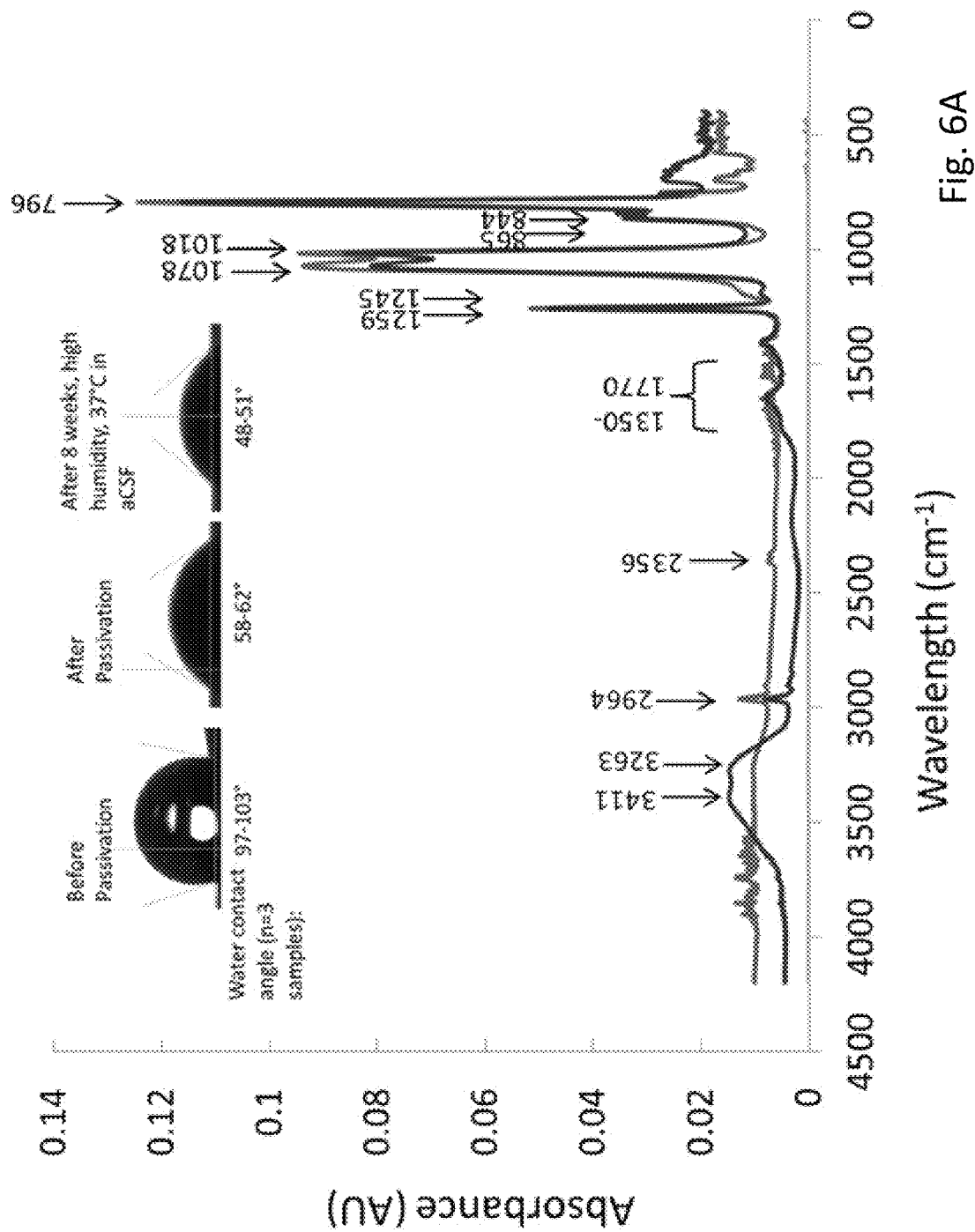
FIG. 6A shows a graph of the absorbance versus wavelength for the soft conductive composition (light line) and conventional PDMS (dark line), and the insert shows the water contact angle of the soft conductive composition.

In one embodiment, the soft, silicone composites can have stable surface passivation and suitable mechanical properties for implantation. These soft interfaces maintain their surface passivation properties over 8 weeks in aCSF (FIG. 6A). It should be noted that the elastic modulus of the soft silicone composite was not significantly different after 4 weeks in aCSF, suggesting stability in their mechanical properties under simulated body-conditions (FIG. 4A). In addition, soft, brain-like silicone/CNT composites are conducive to growth of cortical neurons with increased viability and neurite differentiation exhibited by increased branching complexity (FIG. 6B). In FIG. 6A, the FTIR-ATR fingerprint regions of the brain-like conductive composite, where the lighter lines indicate the brain-like conductive composite and the darker lines represent the spectra for conventional PDMS substrates. Arrows indicate wavelength regions that typically characterize the soft, brain-like composite material and conventional PDMS. Inset shows water contact angle analysis of the soft, brain-like composites. Prior to surface passivation treatments, the contact angle is high (FIG. 6A, top left) compared to the contact angle after passivation (top middle). The surface properties remain similar after 8 weeks of immersion in aCSF under simulated body-like conditions (top right). FIG. 6B shows the comparison of cortical neuron growth on soft versus 'hard' composite substrates, where dissociated rat cortical neurons (E18) were seeded and grown for 7 days on soft (5 kPa) and 'hard' (176 kPa) substrates. The cell viability on soft substrates (left) were significantly higher compared to 'hard' composite substrates (right), where soft substrates had approximately 154±37 cells/mm$^2$ and 'hard' substrates had approximately 76±36 cells/mm$^2$. Bar indicates 50 μm.

The relatively stable, electrical interface is also seen with minimal changes in the complex impedance spectra for coated tungsten electrodes after 5-7 weeks of implantation. In comparison, 4 of 6 uncoated tungsten electrodes become resistive after 5-7 weeks of implantation.

The soft brain-like coating increases the impedance at 1 kHz to ~5×106Ω, which is still within the acceptable range for recording electrodes. For soft-coated, platinum-iridium electrodes, the impedance at 1 kHz increases to ~3.8×106Ω. The dip-coated thickness of the soft coating at the interface ranges from 50-150 μm, but the thickness can be smaller or larger.

It was found a soft interface whose viscoelastic properties are matched with that of surrounding brain tissue results in stable electrical impedance at 1 kHz over 5-7 weeks. In addition, 3 of 4 coated tungsten electrodes maintained low impedances over 6 months of implantation and 2 of 4 coated tungsten electrodes maintained low impedances over 432 days of implantation, with only modest increases in electrical impedance in the remaining 2 of 4 after 432 days. In addition, soft-coated platinum-iridium electrodes maintained low impedances in 12 of 16 electrodes over 5 months of implantation. The soft, brain-like coating therefore stabilizes electrical impedance at 1 kHz at the neural interface in vivo. Additionally, FESEM based imaging of soft-coated electrodes post >1 year of implantation showed no discernable pitting or corrosion in the underlying tungsten. No visible loss or degradation of the soft coating was observed in long-term studies. Data showed that the implants remained relatively stable over 1 year for implanted electrodes.

Figure 7:
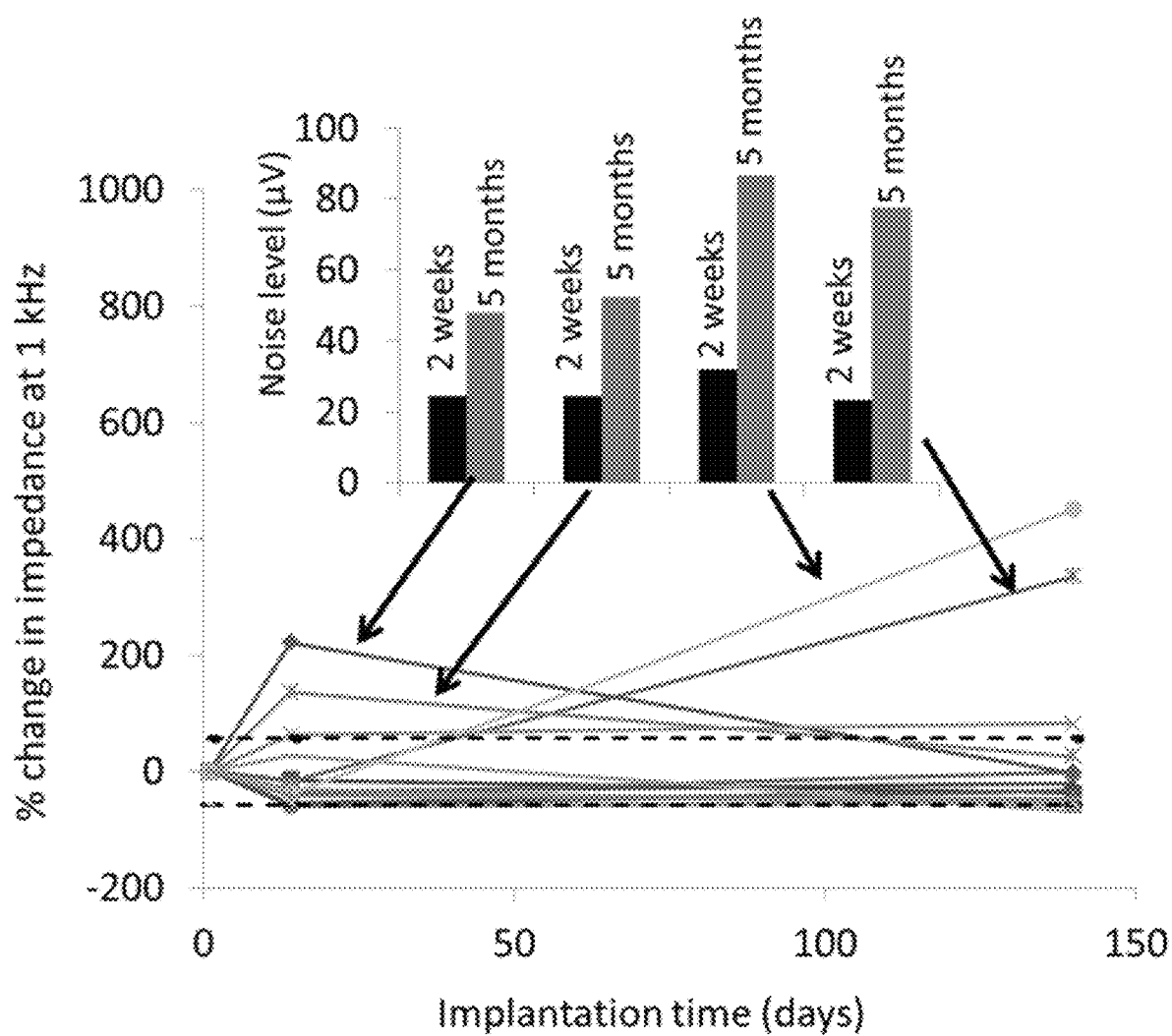
FIG. 7 includes graphs that show the percent change in impedance at 1 kHz for implantation time, and noise level for different implantation times for the soft conductive implant (dark bars) compared to conventional hard composite (light bars).

The relative stability in electrochemical impedance is also reflected in the relative stability of noise levels or floors for over 6 months in soft coated electrodes. In the soft-coated platinum-iridium array, 10 of 16 showed relatively stable noise floors (<15% change over 5 months). 2 of 16 electrodes showed increased impedances (>+150%) after 2 weeks, while 2 other electrodes showed +335 and +450% increase after 5 months. In all 4 cases where an increase in electrical impedance at 1 kHz was observed, it was accompanied by an increase of >50% in relative noise floor levels after 5 months (FIG. 7). 2 of 16 electrodes that showed no significant change in impedance but had increased (>150%) noise levels at 5 months could possibly be due to cell turnover (i.e., cell migration). Further analysis reveals that the above 2 electrodes also exhibit significantly decreased signal to noise ratios (SNRs) at 5 months supporting the earlier speculation about cell turnover.

It was found that single unit neural recordings can be isolated and obtained from soft silicone/CNT composite coated tungsten and Pt/Ir electrodes over durations lasting 5 months to over a year of implantation. Overall long-term signal quality in terms of SNR are similar for both soft-coated and uncoated electrodes. In the soft-coated, platinum-iridium implants, the soft-coated electrodes implanted in the barrel cortex recorded unit activity upwards of 200 μV in amplitude. The SNR increased nearly 1 dB during stimulation of whiskers. In contrast, SNRs obtained during spontaneous or passive periods of activity showed a mixed response across the 16 channel array over implantation time with 50% of electrodes increasing in SNR (>+0.5 dB) at 5 months and 30% decreasing (−0.5 dB) in SNR.

EXPERIMENTAL

PDMS precursors (Sylgard 184 elastomer kit, Dow Corning) were used to fabricate the soft, elastomeric composites. The ratio of base-to-crosslinker as provided in the Sylgard 184 kit was varied until the viscoelastic properties of the resultant elastomer composite with carbon nanotubes matched the viscoelastic properties of rodent brain tissue in vivo. In a prior study, we had shown that pristine cortical brain tissue had typical elastic moduli of around 3-10 kPa with shear moduli around 1.4-3 kPa. The soft elastomeric substrate was incorporated with carbon nanotubes (Sigma-652490—single-walled carbon nanotubes, carboxylic acid functionalized 5 nm×500 nm bundles) for enhanced conductivity at <1% w/v. The mixture was rested for at least 20 min under vacuum to get rid of bubbles, after which it was dip-coated on the recording sites of tungsten or platinum-iridium microwire electrodes (Microprobes, Inc., Gaithersburg, Md.). The bulk resistivity (ρ) of the final, crosslinked-brain-like coating was estimated to be 31.0-41.3 kΩ-cm. The coated electrodes were placed in a dry incubator (60° C.) with low humidity (<5%) for 18 hours. At this point, the consistency of the cured silicone/CNT composite was such that it exhibits strong hysteresis when touched and pulled by a 32 gauge needle but remained well-adhered to the underlying probe surface. The soft, elastomeric composite with CNT had water contact angles of 97-103° based on goniometry measurements determined by automated instrument software (Rame-Hart, Netcong, N.J.). The coated probes were rinsed in deionized water three times and passivated in aCSF (7.4 g sodium chloride, 2.1 g sodium bicarbonate, 0.17 g sodium phosphate monobasic, 0.19 g magnesium chloride, 4.5 g glucose in filtered, deionized water). Bulk samples of soft, brain-like silicone composites were fabricated in 2.5 cm diameter with a depth of 0.5 cm flat bottom wells and indented 200 μm using a stainless-steel, spherical indentor (4 mm diameter). Force was measured using a 10 g load cell (Futek Inc., Irvine, Calif.). The values for elastic moduli were calculated using a Hertzian model, where the elastic moduli were estimated using Equation 1 for spherical indentors.

For assessing long-term, mechanical stability, samples were placed in artificial cerebrospinal fluid (aCSF) for at least 4 weeks inside an incubator at 37° C., 95-99% humidity, 5% CO2 to simulate body conditions. After 4 weeks, the samples (n=3) were taken out and measured for changes in elasticity and swelling based on gravimetric measurements.

Viscoelastic material relaxation properties were compared for 3 groups: (1) cortical brain tissue (n=4 animals) (2) soft, brain-like silicone/CNT composites (n=4 samples), and (3)

0.5% agarose hydrogels (n=3 samples) composed of 0.5% agarose (w/v) (CAS #9012-36-6) and 0.9% saline. Agarose hydrogels are widely used as brain phantoms. A stainless-steel, conical probe was used to penetrate the material and the material relaxation forces imposed on the probe were measured using a 10-g load cell at a sampling frequency of 54 Hz. The relaxation force curves obtained from the load cell were normalized and fitted to a second order prony series model using the MATLAB curve fitting toolbox and the long-term and short-term relaxation time constants were calculated. No significant differences were observed among the long-term relaxation time constants for the 3 groups.

Soft, brain-like coatings from silicone/CNT composites were prepared and studied. The soft composite material composed of a silicone based material with single-walled or multi-walled carbon nanotubes (CNT) were prepared. The tuning or calibration curve for elastic modulus of the composite material as a function of ratio of silicone base-to-crosslinker is shown in FIG. 4. Pristine cortical brain tissue has typical elastic moduli of around 3-10 kPa with shear moduli around 1.4-3 kPa. Using the tuning curve in FIG. 4 for crosslinker to base ratio, the soft, silicone composite was tuned to match cortical brain with an elastic modulus of approximately 5±3 kPa (n=3 samples) with shear modulus of 1.2-1.4 kPa. Mechanical stability tests were performed by placing these soft, brain-like composites in artificial cerebrospinal fluid (aCSF) under simulated body conditions at 37° C. over 4 weeks (FIG. 4A). The estimated elastic moduli for n=3 samples on day 1 was 4.2±1.3 kPa, and after 4 weeks in aCSF was 2.1±0.8 kPa.

Figure 5A:
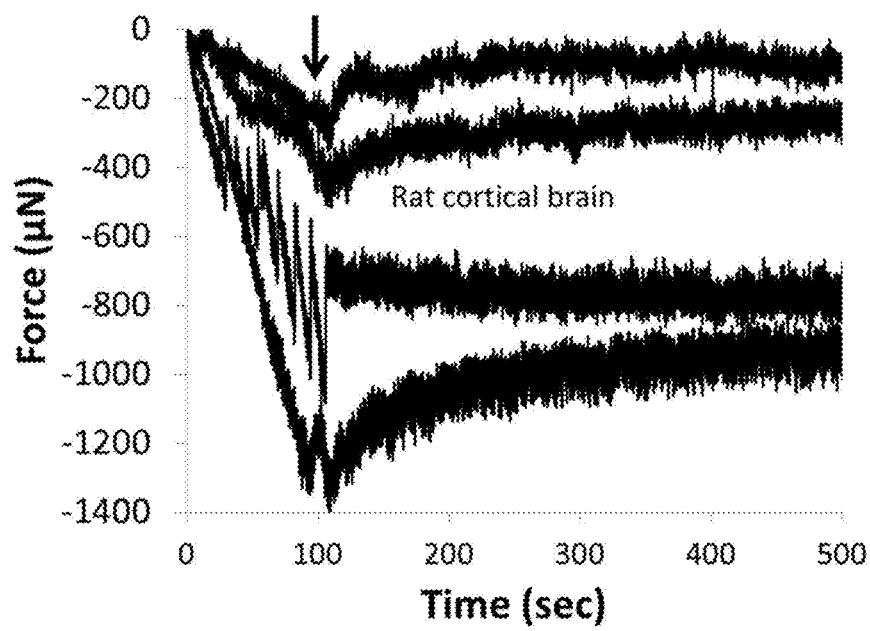
FIG. 5A shows a graph of the force versus time for rat cortical brain tissue.
Figure 5B:
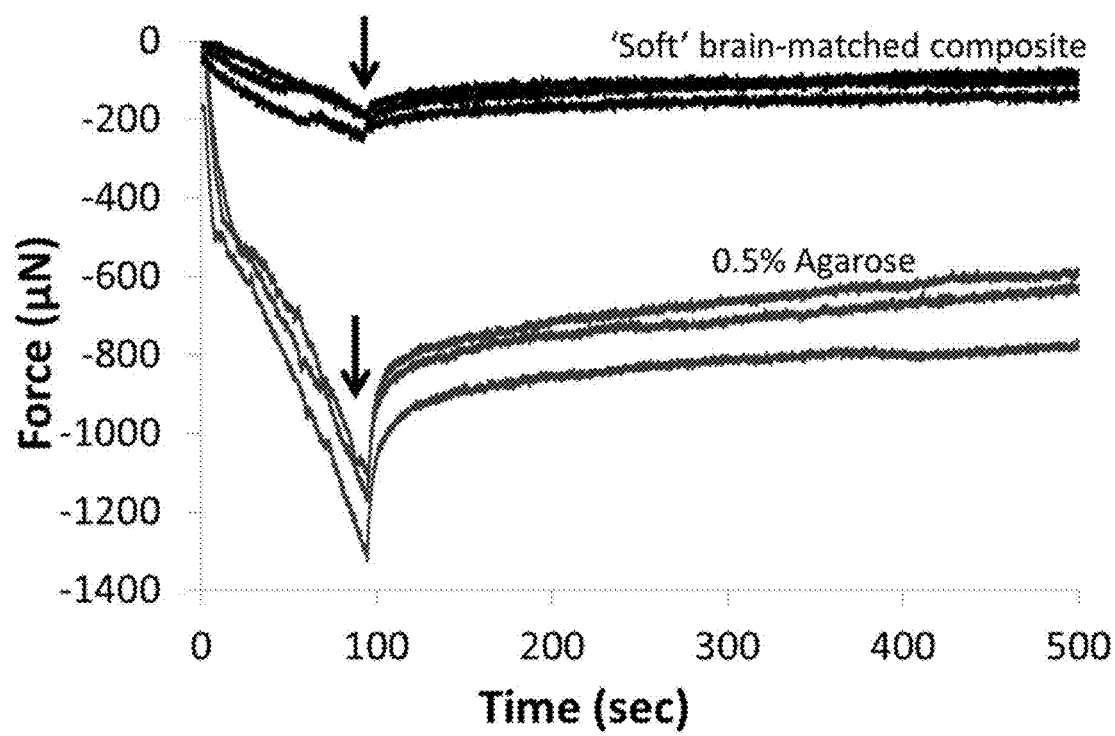
FIG. 5B shows a graph of the force versus time for the soft conductive material and agarose.
Figure 5C:
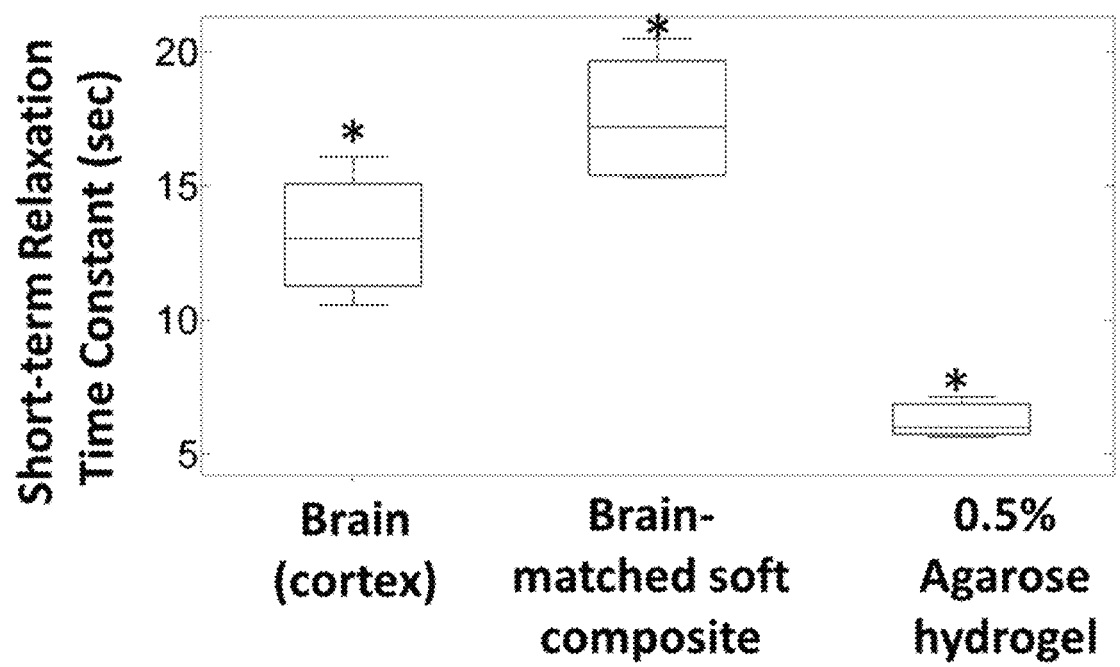
FIG. 5C shows a graph of the short-term relaxation time constant for the brain, the soft conductive material, and agarose hydrogel.
Figure 5D:
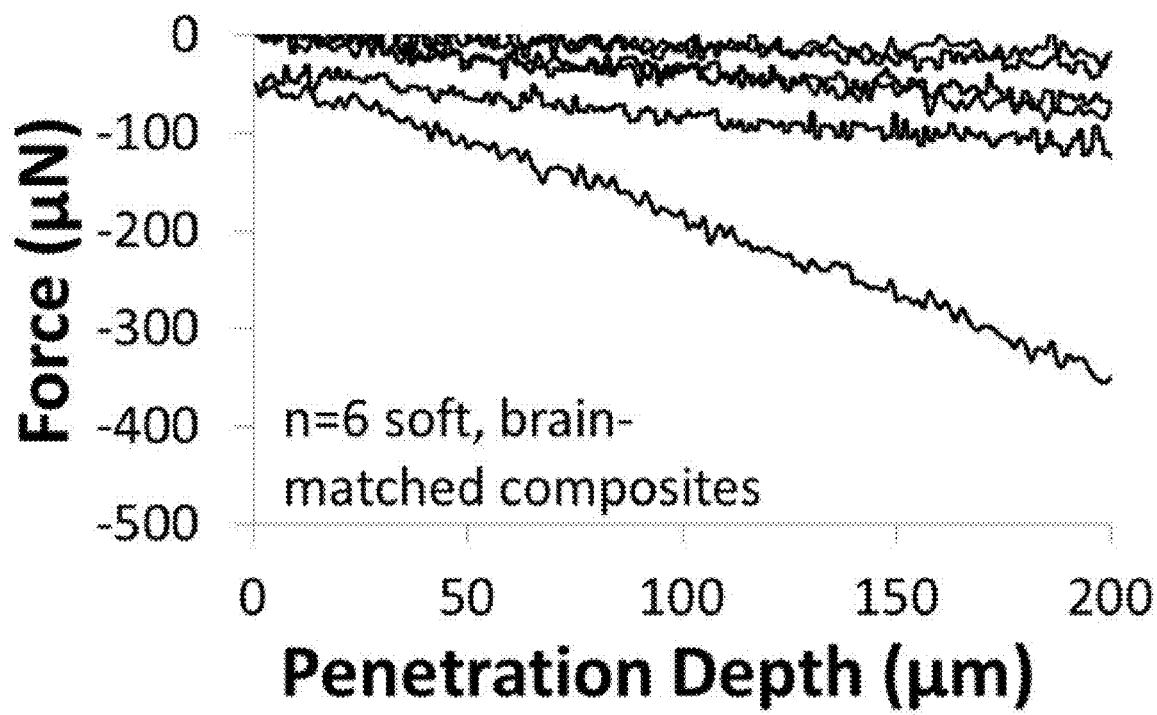
FIG. 5D shows a graph of the force displacement curves for force versus penetration depth for the soft conductive material.
Figure 5E:
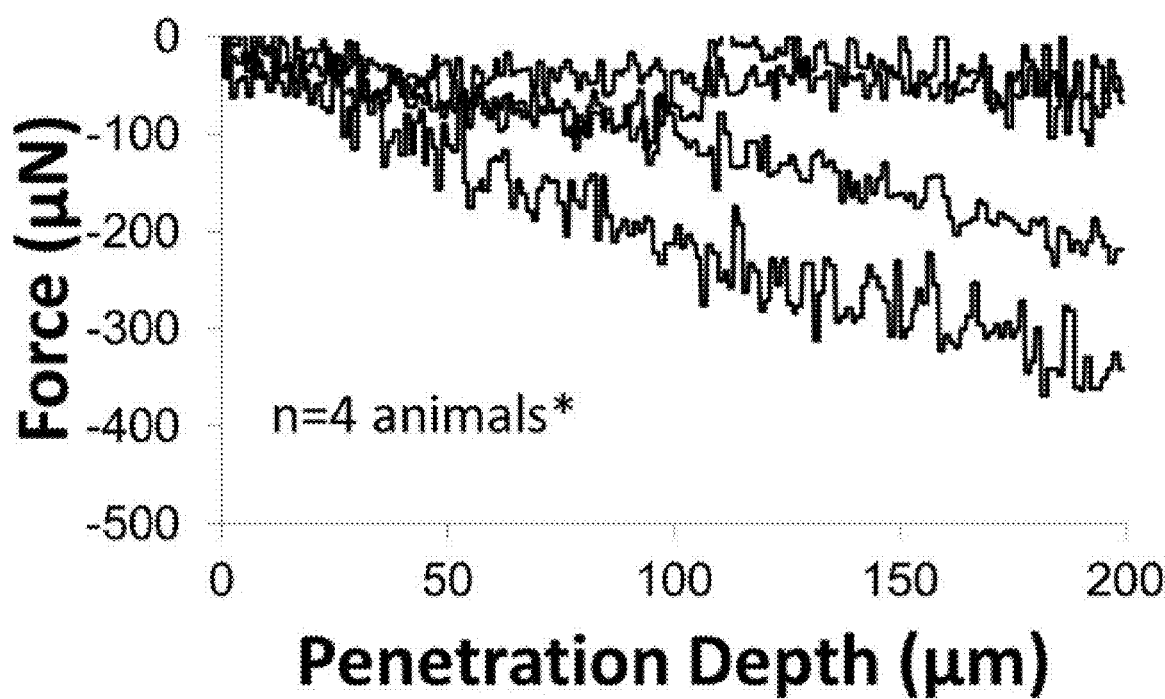
FIG. 5E shows a graph of the force displacement curves for force versus penetration depth for rat cortical brain tissue.

The force-displacement curves using the customized micro-indentation test for cortical brain is shown in FIG. 5A and the corresponding curves for soft, brain-like composite and 0.5% agarose hydrogel (commonly used to model brain phantoms) are shown in FIG. 5B. A stainless-steel conical probe was moved to a depth of 1 mm depth at a speed of 10 µm/s in all of the above 3 materials (characterized by a monotonic increase in compressive force until it reached a maximum of 200-1400 µN), after which all materials exhibited viscoelastic relaxation (characterized by a monotonic decrease in compressive forces at different rates of relaxation). Due to heterogeneity in material parameters, the peak compressive forces in the cortical brain tissue varied over a range and were comparable to those of both the agarose and the soft, silicone composite substrates. The peak compressive forces in soft silicone composites were less than those in 0.5% agarose gel. However, the rate of relaxation of forces was faster for agarose gels compared to those for brain and soft composite material.

Viscoelastic characterization of the soft, brain-like composite showed that the elastomeric material best-fit a second order prony series model typically used to model brain tissue under small strain conditions. The short-term relaxation time constants derived from the prony series model was compared among rat cortical brain, soft silicone composite, and the 0.5% agarose hydrogel as shown in FIG. 5C. The short-term relaxation time constant for the brain tissue was found to be 13.2±2.4 sec. The soft, brain-like composite had a short-term relaxation time constant of 17.5±2.6 sec (n=4 samples), similar to the mean of rat cortical brain. Brain phantoms made of 0.5% agarose hydrogel were found to have a short-term relaxation time constant of 6.25±0.77 sec (n=3 samples). Force-displacement curves generated using a stainless-steel conical probe penetrating (a depth of 200 µm) the soft, brain-like silicone/CNT composite (n=6 samples) and rodent cortical tissue (n=4) are compared in FIGS. 5D and 5E. At a constant movement rate of 10 µm/sec, the force curves were similar in shape with increasing forces observed for both brain tissue and soft, brain-like composite materials. Maximum forces of −61.3±−37.4 µN were observed during penetration in soft, brain-like composites, compared to maximum force values of −173.9±−137.3 µN in rodent cortical tissue. The maximum forces in soft, brain-like composites were not significantly different from those in cortical brain tissue.

Soft, brain-matched silicone composites were fabricated and coated on a silicon (100) wafer substrate. In order to identify and assess the molecular structures on the surface of the novel silicone-CNT composite, FTIR-ATR spectrum was acquired for each material using a Bruker IFS 66V/S IR spectrometer with a wide-band MCT detector cooled by liquid nitrogen under vacuum (courtesy Center for Solid State Science at Arizona State University (CSSS-ASU). The spectrometer was equipped with a germanium ATR crystal (Harrick ATR-GATR); the resolution was 4 cm-1.128 scans were generated and averaged for n=3 samples.

The FTIR-ATR fingerprint spectra of the soft, brain-like composite is compared to that of polydimethyl siloxane (PDMS) in FIG. 6A. FTIR spectra displayed the unique chemical bond vibrational characteristics at specific frequencies for each of the above two materials (indicated by arrows) when stimulated with an infrared (IR) source. In general for PDMS (Sylgard 184), the characteristic peaks were found at 796, 844, 865, 1018, 1078, 1259, 2356, 2964, 3263 cm-1. Different absorbance levels were observed at 2356 cm-1 (—Si—H), 2962 cm-1 (Si—CH3), and 865, 844 cm-1 (Si—OH) for varying degrees of crosslinking that produced a range of elastic moduli. Nanotube incorporation into the silicone network results in modulation of peaks at 1018:1078 cm-1 and addition of a D-band peak at 1245 cm-1, G- and D-band peaks at ~1600 and 1420 cm-1 regions respectively. However, there is some overlap with the PDMS FTIR spectrum for 1300-1800 cm-1 regions with vinyl groups of unreacted crosslinker. The passivation step facilitated the removal of the unreacted crosslinkers and exposed the G- and D-Band regions of nanotubes. In addition, passivation modified the material on the surface with —OH groups (peak at 3411 cm-1) and decreases the —Si—CH2-Si peak at 1078 cm-1. This addition of —OH groups increased the overall surface energy, leading to lower water contact angles as seen in the inset in FIG. 6A. Surface passivation resulted in a decrease in water contact angle from 97-103° to 58-64°. The surface properties were maintained in stability tests where the passivated, soft, brain-like composites that were immersed in aCSF for 8 weeks had water contact angles of 48-51°. Further, gravimetric tests for swelling showed <1% change after 8 weeks of immersion in aCSF. The bulk resistivity (p) of the final, crosslinked-brain-like coating was estimated to be 31.0-41.3 kΩ-cm. Overall, the synergistic combinations of (a) low crosslinking of PDMS leading to low elastic modulus, (b) decrease in exposure of hydrophobic groups (—CH3) and (c) increased exposure of silanol groups (Si—OH) due to nanotube incorporation and surface passivation treatment allows for a highly biocompatible and novel material with flexible functionality for interfacing bioimplants.

Primary cortical neurons (E18 mice) were purchased from Brainbits, LLC, (Springfield, Ill.) and seeded at 5000 cells/mm$^2$ on 'soft' and 'hard' silicone/CNT composite substrates (n=4). Soft (~5 kPa) and hard (~176 kPa) silicone/CNT composite substrates were made by varying the crosslinker-to-base ratio. Substrates were pre-coated with 1 µg/ml polyethyleneimine for 6 hours, washed thrice with sterile distilled water and dried overnight. The neurons were allowed to grow and differentiate at 37° C. and 5% CO2 in NbActiv1 media for DIV 7 (i.e. 7 days in vitro). After 7 days, live assays with Calcein AM (Sigma) were performed and cells were imaged under a fluorescent microscope (488 excitation wavelength). Live cells were counted on each type of 'soft' and 'hard' substrate.

Primary cortical neurons show higher viability on soft substrates in in vitro tests. Dissociated primary cortical neurons were seeded on soft, brain-like silicone composite substrates (~5 kPa elastic modulus) and on 'hard' silicone composites (~176 kPa elastic modulus) (FIG. 6B). After 7 days in vitro (DIV), the cells were imaged using live assay. Neurons cultured on the soft, brain-like substrates had a significantly higher cell viability (154±37 cells/mm2) compared to those on 'hard' substrates (76±36 cells/mm2) ($p<0.05$). In addition, neurite morphology was also different. While the majority of cells on both substrates exhibited primary branching, 17.3% of imaged cells on the soft, brain-like composite substrates had secondary neurite branching compared to 8.8% of the imaged cells on 'hard' substrates.

Customized tungsten array (Microprobes, Llc., Gaithersburg, Md.) with 3 probes (125 μm diameter) that were spaced 1 mm apart were used. A total of 9 tungsten electrodes were coated with the soft, brain-like silicone composite and a total of 6 uncoated tungsten electrodes were used as negative controls. The thickness of the coating varied from 50-150 μm and covered the recording site entirely. In all, n=5 animals were implanted with the tungsten arrays. In addition, one more animal was implanted with a 16-channel-coated platinum-iridium electrode array in the barrel cortex region. Table 2 shows the cohort of animals with details on the length of implantation and the number of coated and uncoated electrodes in each array.

TABLE 2

Experimental details for cohort of rats in this study (n = 6)

| Rat# | Days implanted |
|---|---|
| #1 (3 uncoated tungsten electrodes) | 35 |
| #2 (3 coated tungsten electrodes) | 437 |
| #3 (1 coated, 2 uncoated tungsten electrodes) | 432 |
| #4 (2 coated, 1 uncoated tungsten electrodes) | 35 |
| #5 (3 coated tungsten electrodes) | 49 |
| #6 (16 coated, platinum-electrode electrodes) | 140 |

Briefly, adult CD rats were induced using 50 mg ml-1 ketamine, 5 mg ml-1 xylazine, and 1 mg ml-1 acepromazine administered via intraperitoneal injection. The anesthesia for the update contained a mixture of 50 mg ml-1 ketamine and 5 mg ml-1 xylazine, and was given based on the toe-pinch test. Rats received the analgesic of buprenorphine (0.05 mg kg-1) every 12 hours for 48 hours after surgery was completed. To implant the array, the head of the rat was shaved and the rat was mounted onto a stereotaxic frame (Kopf Instruments, Tujunga, Calif., USA). After the skull was exposed, six stainless-steel bone screws (19010-10 Fine Science Inc., Foster City, Calif., USA) were screwed into the skull to act as anchors, of which two of the screws were also used as grounds. One craniotomy (~3.0 mm diameter) was drilled in the right somatosensory cortex with the center point being 2.5 mm lateral to the midline and 2.5 mm posterior to the bregma. The dura was incised to allow for microarray insertion. The tungsten microelectrode array was slowly inserted into the brain at a rate of 10 μm s-1 and was implanted to a depth of 1.4 mm in the rodent somatosensory cortex for all chronic experiments. The positioning and orientation of the electrode array within the craniotomy was such that one electrode (1) was close to the midline, while electrode (3) was 1 mm lateral to (1) and electrode (2) was 1 mm caudal to (1). For the 16 channel coated, platinum-iridium array, the craniotomy (~5.0 mm diameter) was made in the left somatosensory region centered at 3.0 mm lateral to the midline and 2.5 mm posterior to the bregma. The individual electrodes were spaced 0.5 mm apart in within the array. The array was inserted at a 15° angle to approach the barrel cortex region (~1.0-1.5 mm depth) until whisker stimulated responses were evident in some channels of the array. After the stainless-steel grounding wire was connected to two of the bone screws, gelfoam was placed around the microelectrode array over any exposed brain tissue. After implantation, dental cement (PMMA) was used to secure the array onto the skull.

Electrochemical impedance spectroscopy (1-100,000 Hz) was conducted using a 5 mV amplitude sine wave input signal with CH-660 electrochemical station (CH Instruments, Austin, Tex.) and measurements were used to test for changes in impedance due to tissue remodeling at the electrode-tissue interface. The measurements represented a 2-electrode system with a working electrode and a stainless-ground shorted with the reference. Measurements were done once a week for 5-7 weeks in all animals, at 6 months and 435/437 days for n=2 animals. For the coated, platinum-iridium array implanted in the rat barrel cortex measurements were done up to 140 days in one animal. At least three readings were taken at each time point and averaged and complex impedance spectra (Nyquist diagrams) for all the electrodes were plotted. Impedance measurements at 1 kHz were averaged for each coated and uncoated electrode at each time point and the mean and standard deviation were plotted. The 95% confidence intervals were calculated across all time points for coated and uncoated electrodes and plotted on the respective graphs.

In vivo electrical impedance is more stable for soft coated electrodes. Three-channel tungsten microwire (125 μm diameter) arrays were coated with the soft brain-like silicone/CNT composite at the recording site and implanted in rats. A total of 9 coated, tungsten electrodes and a total of 6 uncoated tungsten electrodes were used as negative controls in 5 different animals. Overall, 2 animals had mixed arrays with both coated and uncoated electrodes, while 1 animal had an array with electrodes that were not coated and 2 animals had all of their electrodes coated with the soft silicone composite. The average initial (day 1) electrical impedance at 1 kHz for uncoated electrodes (n=6) was $1.72\times10^5\pm1.54\times10^5$ ohms and $1.69\times10^6\pm1.91\times10^6$ ohms for soft-coated electrodes (n=9). The median for soft-coated electrodes was $6.2\times10^5\Omega$ compared to $1.3\times10^5\Omega$ for uncoated controls. The larger range for soft-coated electrodes could be due to variations in coating thickness or nanotube distribution or differences in surface passivation.

The measured impedance fluctuated as implantation time increased over 5-7 weeks. Four of 6 uncoated electrodes reached their peak impedance by 14 days of implantation and all 6 uncoated electrodes experienced an increase in impedance within 21 days of implantation. Overall, at its peak, uncoated electrodes experienced +105-280% change in impedance at 1 kHz. At the end of 5-7 weeks, electrical impedance of 3 uncoated electrodes changed +78-150% while electrical impedance of the other 3 uncoated electrodes decreased back to values closer to those on day 1. In contrast, electrical impedance of only 1 of 9 soft-coated electrodes reached a peak increase of 47% in the first 21 days of implantation, while 8 of 9 electrodes were generally stable and experienced low levels of fluctuation in electrical impedance. After 5-7 weeks, electrical impedance of 8 of 9 electrodes remained within +33% of their initial impedance value (95% confidence interval), while the electrical impedance of the other 1 of 9 soft-coated electrodes had +74% change. A total of n=2 uncoated electrodes and n=4 soft-coated electrodes were implanted for >1 year in 2 rats. At the end of approximately 6 months of implantation, electrical impedance of one uncoated electrode increased to 825% of day 1 starting values, while the impedance of the second uncoated electrode increased by a more modest +30%. By >432 days (60+ weeks), impedances of both uncoated electrodes increased further, with one ~+1000% more and the other +272% of original values. In contrast, at the end of approximately 6 months of implantation, 3 of 4 soft-coated electrodes maintained or had lower impedances, while impedance of 1 of 4 electrodes increased to +150% of original impedance value. By >432 days (60+ weeks), 2 of 4 soft coated electrodes maintained or had lower impedances compared to day 1, while electrical impedance of the other two increased to +87% and +150% of day 1 values.

Figure 8:
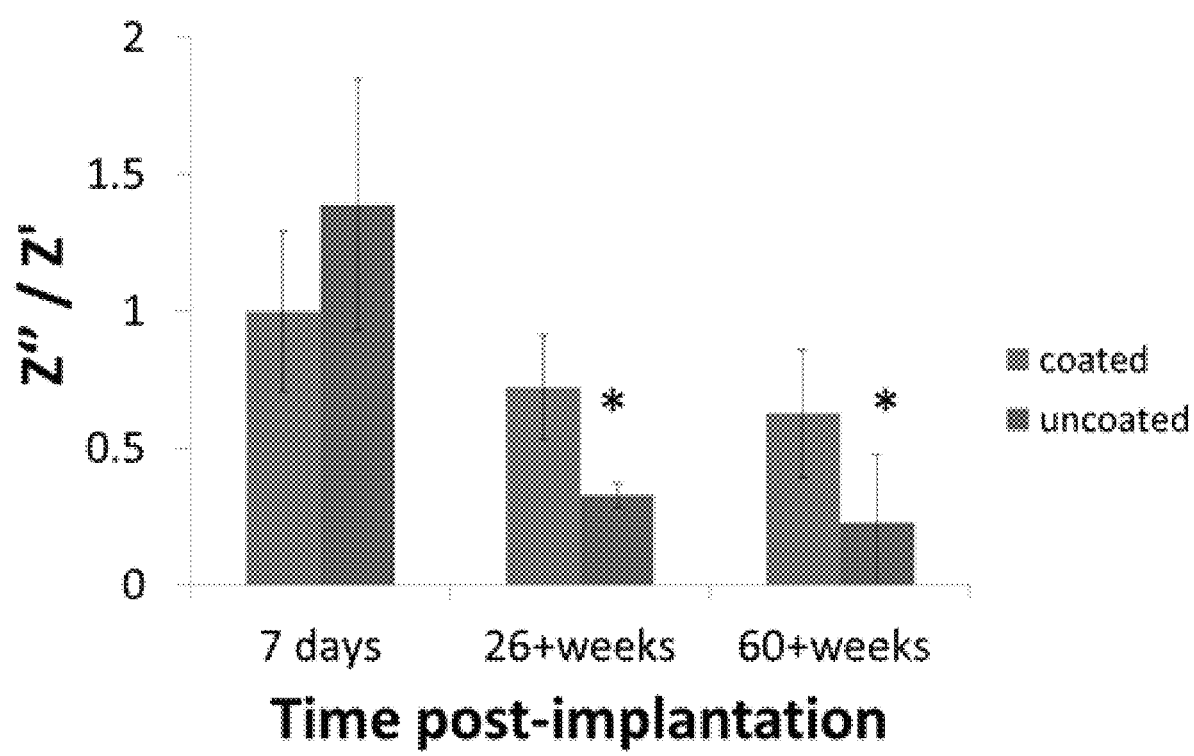
FIG. 8 shows the averaged complex impedance spectra (z''/z') for soft-coated (left bars) and uncoated electrodes (right bars).

Qualitative assessments showed that both uncoated electrodes became more resistive with longer implantation times as observed by a generally decreasing slope trending towards the real-axis (resistance) over 60+ weeks. Similar trends in 4 of 6 uncoated electrodes were observed in Nyquist plots over 5-7 weeks. The other 2 of 6 uncoated electrodes maintained their slopes in Nyquist plots over 5-7 weeks of implantation. In contrast, 3 of 4 soft-coated electrodes maintained their slopes in Nyquist plots over long implantation periods (>60+ weeks). Similar trends were seen in soft-coated electrodes over 5-7 weeks. The Nyquist plot of the soft coated electrode in one soft coated electrode showed more variability within the first 6 months (26+ weeks) having a more resistive slope compared to the one at >1 year (60+ weeks), which had a more capacitive (steeper) slope. Linear fits of the averaged complex impedance spectra showed that the slopes (z"/z') for uncoated electrodes decreased significantly ($p<0.05$), indicative of the spectra becoming more resistive with longer implantation times (FIG. 8). Soft-coated showed no statistically significant change with long implantation times lasting more than 1 year.

In the case of the 16 channel soft-coated Pt/Ir microwire arrays, electrodes were implanted in one animal in the somatosensory region of which 5 electrodes in the array were placed in the barrel cortex region. The average impedances across all 16 electrodes at 1 kHz post-implantation were 3.8 MO (day 1), 3.8 MΩ (after 2 weeks), and 4.9 MO (after 5 months). The relative change in impedance is plotted in FIG. 7 over 5 months of implantation. 75% (12 of 16) of the soft-coated Pt/Ir electrodes had relatively stable impedances over 5 months of implantation. 2 of 16 electrodes showed increased impedances (>+150%) after 2 weeks, while 2 other electrodes showed +335% and +450% increase after 5 months. In all 4 electrodes where impedance at 1 kHz increased >150%, an increase of >50% in relative noise floor levels was also observed after 5 months. Beyond 5 months, the animal was euthanized due to issues unrelated to the implant.

Neural recordings were taken from awake animals using a multi-channel recording system (TDT Inc., Alachua, Fla., USA). Recordings were taken once a week for 5-7 weeks for n=5 rats and at 6 months and at 432/437 days for n=2 rats. For the coated platinum-iridium array implanted in the barrel cortex, recordings were taken at 1 week, 4 months, and 5 months post implantation. The aim was to record neuronal responses to mechanically stimulated whisker activity under long-term conditions using coated electrodes. The whiskers were stimulated using a custom built air-puffing system that was triggered using the TDT system (TDT Inc., Alachua, Fla.) at 1 Hz for 50 msec on-time. Post-stimulus histograms (PSTH) of at least 50 trials were created to assess neuronal responses.

Each recording session was approximately 30 min. The neural signals were sampled at 24.4 kHz and bandpass filtered from 300-3000 Hz, with a gain of 10,000. The recording system was connected to the microelectrode array via a headstage with matching Omnetics™ connector, which was then routed through an A/D converter. Continuous raw data were recorded and analyzed in MATLAB. Spikes were sorted using a custom program that utilized principle component analysis (PCA) and k-means sorting algorithm to identify and sort spikes. For spike sorting, signal was detected by extracting amplitudes that exceeded 3.5 times the standard deviation of the amplitude distribution. After removal of movement artifacts, signal to noise ratio (SNR) and the average noise floor level were determined at one-second intervals using a MATLAB program. An average SNR for 60 seconds of artifact free data was assessed for each electrode. Points were considered signal for the threshold criterion of any points that was greater than 3.5 times the standard deviation of the amplitude distribution. Points below this threshold were considered noise. The SNR was determined by the ratio of signal power to the noise power.

Finally, neural recordings from tungsten electrodes were taken at different time points over 60+ weeks and assessed for signal quality. To better assess signal quality across the various implantation time points up to 60+ weeks and across all 5 animals with tungsten probes, the noise floor level and SNR were calculated and plotted. Pooling uncoated controls and soft-coated tungsten electrodes across the arrays resulted in 3 animals for each category of uncoated controls and soft coated tungsten electrodes.

Figures 9A, 9B:
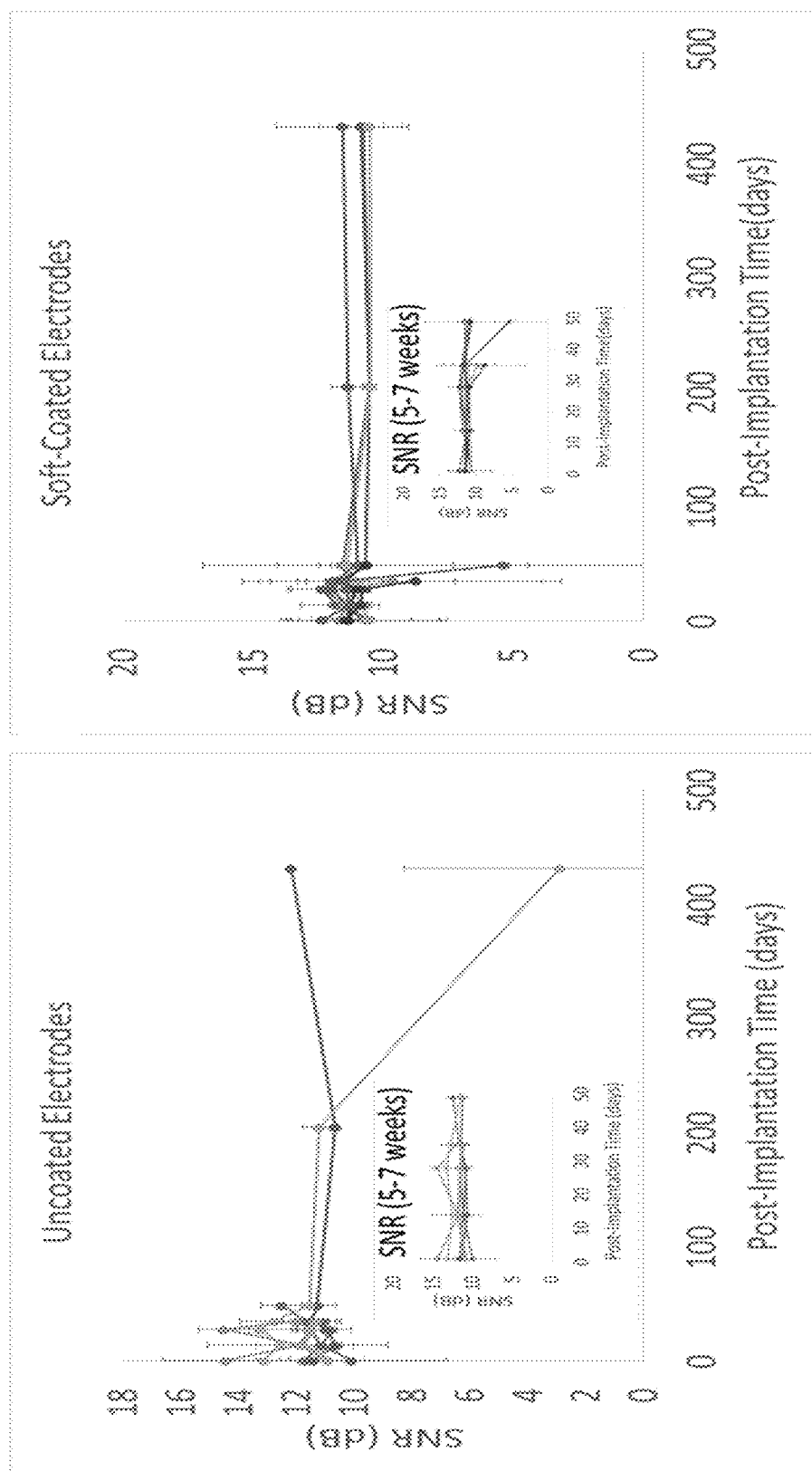
FIGS. 9A and 9B show graphs for the uncoated electrodes (FIG. 9A) and electrodes coated with the soft conductive material (FIG. 9B) for the signal to nose ratio over time.

The maximum peak-to-peak amplitudes in the uncoated tungsten electrodes did not exceed 60 μN, while those from soft-coated electrodes were in the range of 60-150 μN. The SNR (which included all the single units from each electrode) of uncoated controls and soft-coated tungsten electrodes over 1 year are shown in FIGS. 9A and 9B. SNR of uncoated controls (6 tungsten electrodes) had a range of 11.3-12.5 dB, while the SNR in 6 of 9 soft-coated tungsten electrodes was 10.7-11.4 dB after 5-7 weeks of implantation. SNR in the remaining 3 of 9 soft-coated tungsten electrodes decreased significantly to a range of 5.3-9.6 dB after 5-7 weeks of implantation. After 6 months and over 1 year (60+ weeks), the 4 soft coated tungsten electrodes in n=2 animals maintained the SNR levels (10.5-11.6 dB). SNR in 1 of 2 uncoated tungsten controls decreased to 2.9 dB after 1 year (60+ weeks), while the SNR in the other control electrode remained unchanged. For the 16-channel platinum-iridium array, the average SNR across all electrodes after 2 weeks of implantation was 11.3±0.73 dB. After 5 months it remained stable at 11.7±1.24 dB. The noise floor levels at 2 weeks ranged 16.3-32.1 μV for all electrodes. After 5 months, 11 of 16 electrodes remained stable (18.6-36.7 μV).

Typical sorted units resulting from spontaneous activity had ~80-100 μV in peak-to-peak amplitudes after 5 months. While the spontaneous neural recordings were predominantly conducted in passive situations, some soft-coated Pt/Ir electrodes were implanted in the barrel cortex and the neuronal responses to mechanical stimulation of whiskers at 1 Hz. Single and multi-unit responses to whisker stimulation with peak-to-peak amplitudes upwards of 150-200 μV were observed in the soft-coated Pt/Ir electrodes implanted in the barrel region. Relative SNRs increase 0.96 to 1.4 dB due to stimulus related activity in five electrodes within the time period. The timestamps of sorted units show responses to whisker stimulation lasting up to ~100 ms. The earliest response is 19 msec post-stimulus with the peak responses occurring at ~40-50 msec post stimulus.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A conductive composite composition comprising:
a crosslinked silicone composition matrix; and
carbon nanotubes distributed within the crosslinked silicone composition matrix, wherein the conductive composite composition has an elastic modulus of about 2 kPa to about 9 kPa.

2. The composition of claim 1, wherein the conductive composite composition has a short-term relaxation time-constant of about 2 seconds to about 30 seconds.

3. The composition of claim 1, wherein the crosslinked silicone composition matrix includes an anti-inflammatory agent distributed therein.

4. The composition of claim 1, wherein the crosslinked silicone composition matrix has a biocompatible coating thereon.

5. The composition of claim 1, wherein the carbon nanotubes are present up to 5% weight/weight of carbon nanotube weight per silicone base weight, wherein the crosslinked silicone composition matrix is formed from a silicone base and a crosslinker.

6. The composition of claim 1, wherein the carbon nanotubes include carboxylic acid functional groups.

7. The composition of claim 1, wherein the crosslinked silicone composition matrix has an insulation coating thereon.

8. The composition of claim 1, wherein the crosslinked silicone composition matrix is a polydimethylsiloxane (PDMS) silicone.

9. A device comprising:
a medical device; and
the conductive composite composition of claim 1 coating at least a portion of the medical device.

10. The device of claim 9, wherein the medical device is implantable, and the conductive composite composition is on at least an implantable portion of the implantable medical device.

11. The device of claim 10, wherein the implantable medical device includes metal or doped single crystal or polycrystalline semiconductor or carbon, and the conductive composite composition coats at least a portion of the metal or doped semiconductor.

12. The device of claim 9, further comprising an insulation layer between the medical device and the conductive composite composition.

13. The device of claim 11, wherein the metal is selected from the group consisting of stainless steel, platinum, platinum-iridium, silver/silver-chloride, gold, and tungsten.

14. The device of claim 9, comprising one or more of the following:
an anti-inflammatory agent in the conductive composite composition;
biocompatible coating on the conductive composite composition;
the carbon nanotubes being present up to 5% of carbon nanotube weight per silicone base weight, wherein the crosslinked silicone composition matrix is formed from a silicone base and a crosslinker; or
the carbon nanotubes include carboxylic acid functional groups.

15. A method of making an implant, comprising:
crosslinking at least one silicone precursor with a crosslinker to obtain a crosslinked silicone;
introducing carbon nanotubes into the crosslinked silicone to form the conductive composite composition of claim 1; and
coating the conductive composite composition onto at least a portion of an implant.

16. The method of claim 15, further comprising at least one of the following:
degassing/de-bubbling the conductive composite composition;
dry incubating the implant coated with the conductive composite composition under heat; or
curing the conductive composite composition onto the implant.

17. The method of claim 15, further comprising at least one of the following:
rinsing the implant having the conductive composite composition with deionized water; or
passivating the implant having the conductive composite composition.

18. The method of claim 15, comprising controlling the degree of cross-linking the at least one silicone precursor to obtain the elastic modulus.

19. The method of claim 15, comprising:
obtaining a crosslinker to base curve for the crosslinker and at least one silicone precursor;
determining a desired elastic modulus and short-term relaxation time-constant;
determining an amount of the crosslinker for an amount of the at least one silicone precursor; and
crosslinking the at least one silicone precursor with the amount of crosslinker according to the curve to obtain the desired elastic modulus and short-term relaxation time-constant for the conductive composite composition.

20. A method of measuring properties at a neural interface, the method comprising:
providing a neural probe having at least a portion coated with the conductive composite composition of claim 1, the conductive composite composition comprising the crosslinked silicone composition matrix containing the carbon nanotubes;
implanting the neural probe coated with the conductive composite composition at a neural interface; and
measuring a property with the neural probe.

* * * * *